(12) United States Patent
Aboul-Hosn et al.

(10) Patent No.: US 6,532,964 B2
(45) Date of Patent: Mar. 18, 2003

(54) PULMONARY AND CIRCULATORY BLOOD FLOW SUPPORT DEVICES AND METHODS FOR HEART SURGERY PROCEDURES

(75) Inventors: Walid Najib Aboul-Hosn, Sacramento, CA (US); William Russell Kanz, Sacramento, CA (US)

(73) Assignee: A-Med Systems, Inc., West Sacramento, CA (US)

( * ) Notice: Subject to any disclaimer, the term of this patent is extended or adjusted under 35 U.S.C. 154(b) by 293 days.

(21) Appl. No.: 09/231,320

(22) Filed: Jan. 13, 1999

(65) Prior Publication Data

US 2002/0026944 A1 Mar. 7, 2002

Related U.S. Application Data

(63) Continuation-in-part of application No. 09/079,836, filed on May 15, 1998, which is a continuation-in-part of application No. 08/891,456, filed on Jul. 11, 1997, now Pat. No. 6,123,725.

(51) Int. Cl.[7] ............................................. A61B 19/00
(52) U.S. Cl. ........................................ 128/898; 600/16
(58) Field of Search ..................... 128/898; 623/1.15, 623/3.15; 600/16, 17; 604/43, 4, 151; 415/900

(56) References Cited

U.S. PATENT DOCUMENTS

| 3,487,784 A | 1/1970 | Rafferty |
| 3,626,947 A | 12/1971 | Sparks |
| 3,995,617 A | 12/1976 | Watkins et al. |
| 4,086,665 A | 5/1978 | Poirier |
| 4,108,161 A | 8/1978 | Samuels et al. |
| 4,118,806 A | 10/1978 | Poirier et al. |
| 4,173,981 A | 11/1979 | Mortensen |
| 4,548,597 A | 10/1985 | Nelson |
| 4,625,712 A | 12/1986 | Wampler |
| 4,704,121 A | 11/1987 | Moise |

(List continued on next page.)

FOREIGN PATENT DOCUMENTS

| CA | 2037622 | 9/1991 |
| EP | 0 445 782 A2 | 9/1991 |
| EP | 0 478 635 B1 | 4/1992 |
| EP | 0 629 412 A1 | 12/1994 |
| EP | 0 659 443 A1 | 6/1995 |
| EP | 0 768 091 A1 | 4/1997 |
| RU | 286145 | 1/1971 |
| WO | WO89/10763 | 11/1989 |
| WO | WO96/18358 | 6/1996 |
| WO | WO97/02850 | 6/1997 |
| WO | WO97/37698 | 10/1997 |
| WO | WO98/14225 | 4/1998 |
| WO | WO98/53864 | 12/1998 |

OTHER PUBLICATIONS

P.E. Allaire, H.C. Kim, E,H, Maslen, D.B. Olsen, and G.B. Bearnson, "Prototype Continuous Flow Ventricular Assist Device Supported on Magnetic Bearings" *Artificial Organs*, vol. 20, No. 6, 1996 pgs. 582–590, Blackwell Science, Inc. Boston.

*Primary Examiner*—V. Millin
*Assistant Examiner*—Kelly O'Hara
(74) *Attorney, Agent, or Firm*—Jonathan Spangler

(57) ABSTRACT

Pump and cannula systems inserted through the right side and/or left side of the heart provide protection against collapse of the heart chambers and veins and arteries and provide supplemental blood flow through same to enable beating heart bypass surgery on all vessels of the heart, including lateral and posterior vessels. The invention eliminates the use of cardiopulmonary bypass (CPB) machines. The invention further provides stents adapted for protecting from vein, artery, atrium and/or ventricle collapse during beating heart bypass surgery.

48 Claims, 5 Drawing Sheets

U.S. PATENT DOCUMENTS

| | | |
|---|---|---|
| 4,753,221 A | 6/1988 | Kensey et al. |
| 4,769,031 A | 9/1988 | McGough et al. |
| 4,817,586 A | 4/1989 | Wampler |
| 4,846,152 A | 7/1989 | Wampler et al. |
| 4,898,518 A | 2/1990 | Hubbard et al. |
| 4,944,722 A | 7/1990 | Carriker et al. |
| 4,955,856 A | 9/1990 | Phillips |
| 4,985,014 A | 1/1991 | Orejola |
| 5,019,102 A | 5/1991 | Hoene |
| 5,061,256 A | 10/1991 | Wampler |
| 5,112,349 A | 5/1992 | Summers |
| 5,295,958 A | 3/1994 | Shturinan |
| 5,376,114 A | 12/1994 | Jarvick |
| 5,449,342 A | 9/1995 | Hirsoe et al. |
| 5,599,329 A | 2/1997 | Gabbay |
| 5,647,358 A | 7/1997 | Vilasi |
| 5,688,245 A | 11/1997 | Runge |
| 5,718,678 A | 2/1998 | Fleming |
| 5,746,709 A | 5/1998 | Rom et al. |
| 5,755,784 A | 5/1998 | Jarvick |
| 5,766,209 A | 6/1998 | Devonec |
| 5,785,686 A | 7/1998 | Runge |
| 5,827,220 A | 10/1998 | Runge |
| 5,851,174 A | 12/1998 | Jarvick |
| 5,921,913 A | 7/1999 | Siess |
| 5,965,089 A | 10/1999 | Jarvick et al. |

PULMONARY AND CIRCULATORY BLOOD FLOW SUPPORT DEVICES AND METHODS FOR HEART SURGERY PROCEDURES

CROSS-REFERENCE TO RELATED APPLICATIONS

This application is a Continuation-in-Part of copending and commonly owned U.S. patent application Ser. No. 09/079,836, filed May 15, 1998, which is a Continuation-in-Part of commonly owned U.S. patent application Ser. No. 08/891,456, filed Jul. 11, 1997, now U.S. Pat. No. 6,123,725.

FIELD OF THE INVENTION

The present invention is directed to related apparatus systems, equipment and methods for heart surgery procedures.

BACKGROUND OF THE INVENTION

Major heart surgery has been accomplished by procedures that require full cardiopulmonary bypass (CPB), and complete cessation of cardiopulmonary activity. Open heart surgery typically requires significant hospitalization and recuperation time for the patient. The average mortality rate with this type of procedure is low, but is associated with a complication rate that is often much higher compared to when cessation and CPB are not required. While very effective in many cases, the use of open heart surgery to perform various surgical procedures such as coronary artery bypass grafting (CABG) is highly traumatic to the patient. These procedures require immediate postoperative care in an intensive care unit, a period of hospitalization for at least several days, and an extended recovery period. In addition, open heart procedures require the use of CPB which continues to represent a major assault on a host of body systems. For example, there is noticeable degradation of mental faculties following such surgeries in a significant percentage of CABG patients. This degradation is commonly attributed to cerebral arterial blockage and emboli from debris in the blood generated by the use of CPB during the surgical procedure. At the same time, the dramatic increase in the life expectancy of the general population has resulted in patients that are more likely to be older and in poor health, with less cardiovascular, systemic, and neurologic reserve needed to recover from the trauma caused by the use of CPB. As a consequence, inflammatory, hemostatic, endocrinologic, and neurologic stresses are tolerated to a much lesser degree by a significant number of patients today, and play a more significant role in CPB-induced morbidity.

The CABG procedure generally involves open chest surgical techniques to treat diseased vessels. During this procedure, the sternum of the patient is cut in order to spread the chest apart and provide access to the heart. During surgery the heart is stopped, and by the use of CPB blood is diverted from the lungs to an artificial oxygenator. In general CABG procedures, a source of arterial blood is then connected to a coronary artery downstream from the occlusion. The source of blood is often an internal mamary artery, and the target coronary artery is typically among the anterior or posterior arteries which may be narrowed or occluded. The same or similar CPB procedure is used in conjunction with other cardiac surgical procedures, such as value repair or replacement and heart transplant.

The combined statistics of postoperative morbidity and mortality continue to illustrate the shortcomings of CPB. The extracorporeal shunting and artificially induced oxygenation of blood activates a system wide roster of plasma proteins and blood components in the body including those that were designed to act locally in response to infection or injury. When these potent actors are disseminated throughout the body without normal regulatory controls, the entire body becomes a virtual battleground. The adverse hemostatic consequences of CPB also include prolonged and potentially excessive bleeding. CPB-induced platelet activation, adhesion, and aggregation also contribute to a depletion in platelet number, and is further compounded by the reversibly depressed functioning of platelets remaining in circulation. The coagulation and fibrinolytic systems both contribute to hemostatic disturbances during and following CPB. However, the leading cause of morbidity and disability following cardiac surgery is cerebral complications. Gaseous and solid micro and macro emboli, and less often perioperative cerebral hypoperfusion, produce neurologic effects ranging from subtle neuropsychologic deficits to fatal stroke. Advances in computed tomography, magnetic resonance imaging, ultrasound, and other imaging and diagnostic techniques have added to the understanding of these complications. But with the possible exception of perioperative electroencephalography, these technologies do not yet permit real time surgical adjustments that are capable of preventing emboli or strokes in the making. Doppler and ultrasound evaluation of the carotid artery and ascending aorta, and other diagnostic measures, can help identify surgical patients at elevated risk for stroke and are among the growing list of pharmacologic and procedural measures for reducing that risk.

CPB also affects various endocrine systems, including the thyroid gland, adrenal medulla and cortex, pituitary gland, pancreas, and parathyroid gland. These systems are markedly affected not only by inflammatory processes, but also by physical and biochemical stresses imposed by extracorporeal perfusion. Most notably, CPB is now clearly understood to induce euthyroid-sick syndrome which is marked by profoundly depressed triiodothyronine levels persisting for days following cardiothoracic surgery. The efficacy of hormone replacement regimens to counteract this effect are currently undergoing clinical investigation. By contrast, levels of the stress hormones epinephrine, norepinephrine, and cortisol are markedly elevated during and following CPB, and hyperglycemia is also possible.

Alternatives to CPB are limited to a few commercially available devices that may further require major surgery for their placement and operation such as a sternotomy or multiple anastomoses to vessels or heart chambers. For example, some present day devices used in CPB may require a sternotomy and an anastomosis to the ascending aorta for placement. The main drawbacks of these devices include their limited circulatory capacity, which may not totally support patient requirements, and their limited application for only certain regions of the heart, such as a left ventricular assist device. Other available devices that permit percutaneous access to the heart similarly have disadvantages, such as their limited circulatory capabilities due to the strict size constraints for their positioning even within major blood vessels. Moreover, the relative miniaturization of these types of devices present a high likelihood of mechanical failure. In further attempts to reduce the physical dimensions for cardiac circulatory apparatus, the flow capacity of these devices is significantly diminished.

During cardiac surgery, the heart is either beating, in which case the heart continues to circulate the blood through the lungs to maintain the patient, or immobilized entirely in which case oxygenation and circulation of blood to maintain the patient requires use of CPB. Bypass surgery on a beating heart has been limited to only a small percentage of patients requiring the surgical bypass of an occluded anterior heart vessel. These patients typically could not be placed on CPB and were operated on while the heart was kept beating. These patients are at risk of having to be placed on CPB on an emergency basis in the event the heart stops or becomes unstable or is damaged during the surgical procedure on the beating heart. Meanwhile, patients requiring surgery on posterior or lateral heart vessels and whose hearts must be immobilized and placed on CPB often suffer major side effects as previously described.

The medical community is currently performing more beating heart bypass surgery in an effort to avoid the use of artificial heart-lung machines. The need is increasing for apparatus systems, methods and associated equipment to enhance the capability and versatility of beating heart surgery and to avoid CPB procedures in any heart surgery. The current trend toward thoracoscopic methods of performing bypass surgery, without opening the chest cavity, have resulted in limited success and applicability primarily due to the limited number of heart vessels which can be accessed through thoracoscopic methods. A major limitation of thorascopic bypass surgery methods is due to the fact that only the anterior heart vessels are accessible for surgery. More importantly, even open chest surgery providing full access to the heart also requires CPB when bypass surgery is performed on the lateral or posterior vessels of the heart, due to the fact that in conventional procedures the heart must be stopped when it is lifted or rotated from its normal position and manipulated for surgical access to the various heart vessels, Obviously, the heart is also stopped when valve repair or replacement is performed and when heart transplant is performed.

SUMMARY OF THE INVENTION

The present invention provides apparatus systems and methods which enable any cardiac surgical procedure to be performed while using the patient's lungs, or at least one lung, for blood oxygenation. This invention enables the surgeon to perform any beating heart, still heart or heart transplant procedure without the use of CPB or other external blood oxygenation equipment or procedure. In its main aspect, this invention enables such non-CPB heart surgery by providing device systems and methods to assure continued pulmonary blood flow through the patient's lungs or lung and circulatory flow of the oxygenation pulmonary blood through the patient's body at sufficient levels to sustain the patient during the surgery, regardless of whether the heart is beating with sufficient output, beating with insufficient or partial output or is stopped.

This invention provides for internal and/or external device systems for carrying out the methods of this invention, which device systems are selected and used by the surgeon depending on the cardiac surgical procedure to be performed on the patient. The systems of this invention include three basic systems which can be employed individually or in various combinations to meet the needs of a particular surgical procedure. Each of these systems can be selected and employed in the left side or the right side of the heart, either individually or in combination with another of the systems of this invention. As further illustrated in the description of the invention and exemplified in the drawings herein, the device systems can be positioned for optimal blood flow protection and/or augmentation, i.e., blood intake/inlet positioned in the vein, the atrium or the ventricle and the output/outlet positioned in the ventricle or artery.

The first system of this invention comprises a pump and cannula system wherein the cannula is adapted for insertion through the interior of the heart and/or heart valves to an artery. The right side is through the tricuspid valve and/or pulmonary valve into the pulmonary artery; the left side is through the bicuspid valve and/or aortic valve into the aorta. The pump is adapted as a miniaturized blood pump so it can be positioned close to the heart, either in the open chest cavity or at least in the sterile surgical field, thus providing a minimum priming volume. Alternatively, this system can also be adapted to be inserted into the heart in closed chest procedures through the chest wall as part of a thorascopic procedure, through the femoral vein, the jugular vein or any appropriate access point in the venous system. In these instances the pump is adapted to be positioned as close to the body insertion point as possible in order to keep priming volume to a minimum; for that reason thorascopic or jugular access is preferred when a closed chest procedure is elected. This pump and cannula system is optimally used in both the right and left sides when bypass surgery is initiated, and is employed particularly when the beating heart will need to be lifted, rotated or otherwise manipulated to access lateral or posterior blood vessels, when the heart outflow is cut off by a collapse or kink in the heart chambers or in the veins or arteries, or when the heart is stopped for valve surgery, internal surgery or other reason. This system is also desirable in any heart surgery procedure, even for anterior vessel bypass, when lifting or manipulating of the heart is not anticipated. This applies to both open chest and minimally invasive procedures. This system being put in place in the heart before the cardiac surgery begins, thus assures that the patient will at all times during the surgery have adequate pulmonary blood flow through the lungs and circulatory blood flow throughout the body and will avoid the necessity of being placed on a CPB machine in the event of an unexpected failure of the beating heart to sustain adequate pulmonary or circulatory blood flow during beating heart surgery. This system allows the heart to continue to beat and provide pulmonary and circulatory blood flow to the extent it is capable, until there is a collapse, kink, arrhythmia or arrest, which decreases or stops the blood flow output by the heart. When that occurs, the pump(s) in either or both sides of the heart is/are engaged to supplement the heart produced blood flow or replace the blood flow so that the pulmonary and circulatory blood flows are maintained at a sufficient level to sustain the patient for the duration of the surgery. By having this system in place at the beginning of the beating heart surgery, even for anterior vessel surgery when no need is anticipated, it can merely be engaged or turned on to provide pump assisted blood flow if needed on an unexpected or emergency basis, thus assuring that emergency CPB procedures are avoided. Thus, this system assures that the patient's lungs are utilized for oxygenation of the blood during the entire surgical procedure, even if an unexpected interruption in blood flow from the beating heart occurs. The system can be also utilized for still heart or stopped heart CABG procedures, where the heart has been stopped by infusing drugs into the patient's heart, such as cardioplegia or utilizing any other drug that is available that provides the same function. The pump(s) and cannula(s) provide sufficient pulmonary blood circulation to utilize the patient's lungs for oxygenation and sufficient circulatory blood flow to the body. In this regard, it is noted that one lung is normally sufficient to sustain the patient during surgery. In some procedures the surgeon prefers to collapse one lung to provide additional space inside the chest cavity in which to work. This system accommodates such procedure while sustaining the patient on one lung throughout the surgery and avoiding a CPB machine. Likewise, it is sometimes desired by the surgeon to shrink down the heart by evacuating blood from one or more chambers of the heart, also to provide additional space within the chest cavity in which to work. This system likewise accommodates such procedure, because the pump and cannula system sustain adequate pulmonary and circulatory blood flow throughout the surgical procedure. In this system of this invention the pump in each side is a variable output pump from zero to maximum and is controlled automatically or manually in response to appropriate measurement of blood pressure, blood flow, blood oxygen level, blood $CO_2$ level and/or other desired parameter.

In a second system of this invention, beating heart support is provided to prevent kinking, collapse or undue restriction of blood flow through the beating heart while the heart is manipulated during surgery. This system of devices comprises cannulas and/or stents adapted to be placed in the heart chambers and in the venous and arterial vessels proximate to the heart and in those areas or zones where collapse or kinking during manipulation of the beating heart during surgery is likely to cause restriction in desired pulmonary and/or circulatory blood flow. The devices are placed as desired before or during surgery to allow the beating heart to provide at least a minimum but sufficient pulmonary and circulatory blood flow during surgery. Even when kinking, restriction or collapse of a vein, artery or heart chamber occurs during surgery, the beating heart is still provided a protected passageway equal to the inside diameter of the cannula or stent through which the heart can provide blood flow. In this system no pump is provided and the blood flow is provided solely by the beating heart. By protecting the blood path from restriction or collapse, this system assures the output of the beating heart is available at all times during the surgery to sustain the patient during surgery with sufficient pulmonary and circulatory blood flow. As is apparent, this system is adapted for use exclusively in beating heart procedures. The various types of cannulas/stents with and without check valves and the placement thereof are described in detail below. As mentioned above in connection with the first system of this invention, this second system can be used in conjunction with procedures involving collapsing one lung and/or partially reducing the size of the beating heart to provide additional space in the chest cavity in which the surgeon can work.

The third system of this invention is similar to the above first system in that it comprises a pump and cannula system but is adapted to be placed external of the heart instead of internal in the heart. In this system an intake cannula is adapted for receiving blood from the vein, atrium or ventricle and for passing the blood to the pump, where the blood is passed to an outlet cannula adapted to pass the blood into the artery, all external of the heart. The pump and cannula combinations of this system can be adapted for use in minimally invasive procedures, but are optimally adapted to be miniaturized for placement within the chest cavity or at least within the sterile surgical area to provide a minimum priming volume of the pump and cannula system. This system is optimally used in open chest procedures where the heart will be stopped, such as for value repair or replacement, septum repair or heart transplant. As mentioned above in connection with the first system of this invention, this third system can be used in conjunction with procedures involving collapsing one lung and/or reducing the size of the heart by partially or substantially evacuating one or more chambers of the heart to provide additional space in the chest cavity in which the surgeon can work. As is apparent, this system employs the same type of variable output pump and is controllable in the same manner as in the above first system. This system is adapted to provide sufficient pulmonary and circulatory blood flow in the patient during surgery by either supplementing the beating heart output and/or replacing or substituting for the heart output. This system is adapted to assure sufficient pulmonary and circulatory blood flow and to assure no need for a CPB machine or procedure.

This invention further provides that the above three systems can be selected separately for use in or for the right side and left side of the heart for any particular procedure. For example, the external third system might be used for the right side, while the second or first system is used for the left side, whereby the combination of the two provides sustained and sufficient pulmonary and circulatory blood flow during the cardiac surgical procedure in question. Conversely the external third system might be used for the left side, while the second or first system is used for the right side. One skilled in the art can select the appropriate combinations of the systems following the teaching herein for providing sufficient pulmonary and circulatory blood flow, while avoiding any need for a CPB machine or procedure. Any combination of the three systems could be used in a beating heart, still heart, or when the heart is in any condition there between where the heart is slowed but not completely stopped during the surgical procedure.

The first and second systems and methods of this invention enable beating heart bypass surgery by providing apparatus for protecting the right side from collapse or other restriction, such as ineffective pumping due to heart muscle stress or compression, in order to maintain at least partial pulmonary blood flow through the beating heart, apparatus for augmenting or supplementing the pulmonary and/or circulatory blood flow with a blood pump/cannulation system having a minimum priming volume and, optionally, apparatus for supporting the beating heart in a lifted or manipulated position for bypass surgical access to heart vessels. When desired, the systems and methods of this invention can optionally include apparatus for protecting the left side from collapse to maintain at least partial aortic blood flow through the beating heart and apparatus for supplementing or augmenting the aortic blood flow with a blood pump system having a minimum priming volume. However, in some instances, the aortic circulatory blood flow through the left side of the heart can be sufficiently maintained during beating heart surgery without protecting the left side or supplementing or augmenting the aortic blood flow through the beating heart.

In reference to this invention, "right side" refers to and includes the vena cava veins, the right atrium, the right ventricle, the pulmonary artery and any combination or all thereof, and is referred to as providing the pulmonary blood flow through the lungs. Similarly, "left side" refers to and includes the pulmonary veins, the left atrium, the left ventricle, the aorta and any combination or all thereof, and is referred to as providing the circulatory blood flow through the body. Also, as used herein vena cava includes superior and inferior vena cava, pulmonary artery and vein includes branches thereof and aorta includes the aortic vessels which are near the heart and are exposed or manipulated during open chest cardiac surgery or are utilized during minimally invasive cardiac surgery.

A major obstacle to performing beating heart bypass surgery on lateral or posterior heart vessels is that when the beating heart is lifted or manipulated to provide surgical access to the lateral or posterior heart vessels, the right side, i.e., the right atrium, or the right ventricle, or both, tends to collapse or diminish in pumping capacity and pulmonary blood flow diminishes to an unacceptably low level and/or the pulmonary artery tends to collapse, kink or become otherwise unduly constricted while the heart is displaced or manipulated. This invention provides apparatus systems and methods for protecting the right side and through the lungs and for maintaining and/or supplementing pulmonary blood flow through the right side and through the lungs while the beating heart is lifted and manipulated for full surgical access to lateral and posterior heart vessels, thus enabling unrestricted beating heart bypass surgery.

In one aspect, this invention provides a system for preventing collapse of the vena cava, right atrium, right ventricle and/or pulmonary artery during beating heart bypass surgery comprising a pump and cannula system wherein the cannula portion is adapted for insertion through the tricuspid valve, through the pulmonary valve and a sufficient length into the pulmonary artery to prevent collapse of the right atrium, right ventricle and/or pulmonary artery and to maintain at best partial blood flow therethrough by the beating heart pumping action while the beating heart is lifted or displaced during surgery. Access for insertion of the cannula portion can be through the vena cava, e.g., from a femoral vein incision, through an incision in the wall of the vena cava or in the wall of the right atrium. If the cannula is not inserted through the tricuspid valve, but only through the pulmonary valve and into the pulmonary artery, access could be through an incision in the wall of the right ventricle or reverse access can be used by entering through an incision in the wall of the pulmonary artery. Separate cannulas can be employed, i.e., one introduced through the right atrium and through the tricuspid valve but ending in the right ventricle, and a second introduced by any desired access and beginning in the right ventricle and extending through the pulmonary valve and a desired length, according to this invention, into the pulmonary artery. The pump portion of the system is adapted for intake of blood upstream of the pulmonary valve or upstream of the tricuspid valve and output of blood into the right ventricle or into the pulmonary artery while the beating heart is displaced during surgery. The pump system is preferably integral with the above cannula or cannulas, particularly in a concentric double wall cannula configuration, or can comprise pump cannulas separate from and in addition to the above cannulas which protect the right side from collapse. The optional cradle system is adapted for supporting the beating heart while the heart is displaced and for providing surgical access to lateral or posterior heart vessels.

In another aspect, this invention further provides an optional embodiment which, in addition to the above system for the right side, a separate pump and cannula system is provided for the left side wherein the cannula portion is adapted for insertion through the bicuspid valve, through the aortic valve and a sufficient length into the aorta to prevent collapse of the pulmonary vein, left atrium, left ventricle and/or aorta and to maintain blood flow therethrough by the beating heart pumping action while the beating heart is lifted or displaced during surgery. As indicated above for the right side, access for the left side cannula or cannulas can be from any desired upstream or downstream incision. One or two cannulas may be employed for preventing collapse of the left side and the pump portion of the system, which may have its separate cannulas, is adapted for intake of blood upstream of the aortic valve or the bicuspid valve and output of blood into the left ventricle or the aorta while the heart is displaced during beating heart surgery.

As is apparent, either the right side system or the left side system or both may be used for a particular patient or procedure. Whether the cannula for pump output extends into the pulmonary artery/aorta or extends only into the respective ventricle will similarly depend on the requirements for a particular patient or procedure. In some instances the beating heart blood flow is impeded due to partial compression, wrinkling or other distortion of the ventricle muscle. Although the muscle is working, it is unable to both fill the ventricle with blood and expel or pump the blood in sufficient quantity. The pump system of this invention can be used by positioning the pump cannula output end in the ventricle to fill or preload the ventricle with blood, so the heart muscle can then pump or expel the blood from the ventricle, even though the muscle is not in its normal shape or position. In this aspect of the invention, beating heart blood flow can be maintained while the heart is displaced during surgery without the necessity of the cannula extending through the pulmonary/aortic valve. The heart may be stopped by short acting drugs that which stop the heart for a short period of time, or by electrical means affecting the electrical conduction of the heart or neurological systems or by use of electrical current to paralyze the nerves responsible for heart beating. While the heart is stopped, the pump(s) will deliver 100% of the necessary blood pulmonary blood flow to and from the lungs and/or 100% of the necessary circulatory blood flow to and from the body without any assistance from the heart. In the event the heart is stopped, and particularly when the heart is opened (such as for valve surgery), it is preferred to provide a seal by balloon sheath cannula, clamp or otherwise to isolate the heart, or at least one side of the heart, at the intake cannula and output cannula so that the pumped blood is directed from the vein to the artery without leakage or backflow into the heart during the surgery. This will enhance the pulmonary and/or circulatory blood flow provided by the pump in the pump and cannula system.

In another aspect, this invention provides a pump and cannula system for use in heart surgery wherein the pump and its cannula system have a priming volume less than about 1,000 ml. Optimally, each individual pump/cannula unit will have a priming volume less than about 100 ml and preferably less than about 50 ml. In one preferred embodiment, the pump and cannula system comprises concentric intake and output conduits, a coaxial cannula, adapted for insertion into a single incision. In another preferred embodiment of this aspect of the invention, the pump and cannula system comprise an intake cannula for insertion in the upstream vessel or heart chamber and an output cannula for insertion downstream into the pulmonary artery or the aorta. In a further preferred embodiment of this aspect the pump and cannula system comprises a miniaturized pump having a sterile drive motor suitable for placement of the pump including the drive motor close to the chest and in the sterile zone, or preferably within the chest cavity itself during the heart surgery. In a further preferred embodiment of this aspect a preferred pump is a reverse flow pump and coaxial cannula combination having a minimum priming volume is used, but a cable driven axial flow pump or other conventional blood pump can be used in this invention.

In another aspect, this invention provides a cannula system for protecting selected portions or all of the right side from collapse during beating heart surgery, an optional cannula system for protecting selected portions or all of the left side from collapse and optional pump and cannula systems for use with the right and/or left side protection cannulas, if needed to supplement or augment the blood flow provided by the beating heart. In some patients all that may be required is the protection cannula or cannulas in the right side to allow the beating heart to maintain sufficient pulmonary and circulatory blood flow during the beating heart bypass surgery and it may not be necessary to use the pump system to provide supplemental pulmonary blood flow and may not be necessary to protect the left side or to provide supplemental circulatory blood flow. For such patients, this invention enables beating heart bypass surgery without artificial pumping of the blood and with minimum invasive apparatus. In some patients, beating heart bypass surgery can be started or attempted with only right side protection cannula(s) in place, then right side supplemental pumping of pulmonary blood flow added during the bypass surgery (or after the surgery) by separately inserting the pump system according to this invention. Likewise, left side protection cannula(s) and/or left side supplemental pumping of arterial blood can be added as needed during (or after) the bypass surgery by insertion of the cannula(s) and/or pump systems according to this invention. Thus, this invention provides optional incremental apparatus that may be selected by the surgeon and used only according to particular patient needs in order to minimize the invasiveness of the bypass surgery procedure.

In another aspect, this invention provides for beating heart surgery a valved cannula having an outside diameter adapted for positioning in the right ventricle through the pulmonary valve and in the pulmonary artery, having blood inlet in the ventricle portion, a blood outlet in the artery portion, a one-way valve or check valve between the inlet and outlet adapted to allow blood flow substantially only in one direction from the inlet toward the outlet and a positioning lead attached to the cannula for holding the cannula in proper position in the heart and the pulmonary artery. This pulmonary valve cannula is adapted to receive blood through the inlet from the right ventricle when the right ventricle contracts and expel the blood through the outlet in the pulmonary artery. The one-way valve is adapted to prevent significant back flow of blood through the cannula back into the right ventricle. The cannula may be adapted and sized to allow blood to flow between the pulmonary valve and the external surface of the cannula when the right ventricle contracts and to allow the pulmonary valve to substantially seal to the external surface of the cannula and prevent significant back flow of blood around the cannula back into the right ventricle, when the right ventricle expands. The portion of the cannula contacting the pulmonary valve can be a different outside diameter than the ventricle portion or the artery portion of the cannula, or both. It may be desirable in some patients to have the outside diameter of the cannula at the pulmonary valve contact portion smaller to allow the maximum beating heart blood flow around the outside of the cannula when the pulmonary valve opens. In other patients it may be desirable to have a larger diameter to maximize the beating heart blood flow through the cannula as opposed to around the cannula. The inlet and outlet can be conventional blood cannula configurations and/or can comprise orifices, slits or other openings at desired locations and intervals along portions of the length of the cannula. The ends or openings can comprise baskets, cages or other guards to prevent suction of heart tissue or blood vessel wall into the cannula. The internal valve in the cannula can be any suitable one-way or check valve, such as a flap valve, slide valve, spring loaded circular valve or ball valve, membrane valve, duck bill valve or other design and can be any material appropriate for a blood flow valve. The positioning lead can be attached to the cannula in any desired way and any desired location and adapted for holding the cannula in position during use. The lead can also be useful in inserting and guiding the cannula through the appropriate vessel incision into proper position. The cannula can be inserted with a guide wire/balloon arrangement from an upstream incision.

In another aspect, this invention provides for beating heart surgery a valved cannula having an outside diameter adapted for positioning in the right atrium through the tricuspid valve and in the right ventricle, having a blood inlet in the atrium portion, a blood outlet in the ventricle portion, a one-way valve or check valve between the inlet and outlet adapted to allow blood flow substantially only in one direction from the inlet toward the outlet and a positioning lead attached to the cannula for holding the cannula in proper position in the heart. This tricuspid valve cannula is adapted to receive blood through the inlet from the right atrium and expel the blood through the outlet in the right ventricle when the right ventricle expands. The one-way valve is adapted to prevent significant back flow of blood through the cannula back into the right atrium when the right ventricle contracts. The cannula is preferably adapted and sized to allow blood to flow between the tricuspid valve and the external surface of the cannula when the right ventricle expands and to allow the tricuspid valve to substantially seal to the external surface of the cannula and prevent significant back flow of blood around the cannula back into the right ventricle when the right ventricle contracts. The portion of the cannula contacting the tricuspid valve can be a different outside diameter than the atrium portion or the ventricle portion of the cannula, or both. It may be desirable in some patients to have the outside diameter of the cannula at the tricuspid valve contact portion smaller to allow the maximum beating heart blood flow around the outside of the cannula when the tricuspid valve opens. In other patients it may be desirable to have a larger diameter to maximize the beating heart blood flow through the cannula as opposed to around the cannula. The inlet and outlet can be conventional blood cannula configuration and/or can comprise orifices, slits or other openings at desired locations and intervals along portions of the length of the cannula basket or cage to prevent heart tissue suction. The ends or openings can comprise baskets, cages or other guards to prevent suction of heart tissue or blood vessel wall into the cannula. The internal valve in the cannula can be any suitable one-way or check valve, such as a flap valve, slide valve, spring loaded circular valve or ball valve, membrane valve, duck bill valve or other design and can be any material appropriate to a blood flow valve. The positioning lead can be attached to the cannula in any desired way and any desired location and adapted for holding the cannula in position during use. The lead can also be useful in inserting and guiding the cannula through the appropriate vessel incision into proper position. The cannula can be inserted with a guide wire/balloon arrangement from an upstream incision.

In another aspect of this invention, the above pulmonary valve cannula and the above tricuspid valve cannula may be combined or formed as a single cannula adapted to the position through both the tricuspid and pulmonary valves with the respective check valves, inlets and outlets properly positioned according to the functions set forth above for each. The advantages of this single cannula configuration include single incision, single guide wire and single positioning lead.

In another aspect, this invention provides apparatus for supporting and preventing collapse of the kink zone in the pulmonary artery. In addition to apparatus for supporting and preventing collapse of the right atrium and right ventricle, this invention provides a separately adapted stent to prevent collapse or kinking of the pulmonary artery to maintain blood flow through the pulmonary artery and/or through the stent during beating heart bypass surgery. When the beating heart is lifted and manipulated for surgical access to the posterior or lateral blood vessels, the pulmonary artery tends to fold or kink and restrict or stop the beating heart blood flow. A clamp or stabilizer can be applied to the external surface of the heart to take in the slack from the heart muscle and allow the muscle to function and to generate the contraction to eject blood even if the heart muscle is wrinkled.

As used herein the pulmonary artery "kink zone" is the portion of the pulmonary artery between the heart and the lungs where the artery tends to fold, kink or restrict when the beating heart is lifted or manipulated for surgical access to the lateral or posterior heart vessels. This kink zone is in the portion of the pulmonary artery within about 15 cm from the heart and usually within about 10 cm.

In this aspect of the invention, the pulmonary artery stent is adapted to have diameter and length appropriate to extend the length of the kink zone and an appropriate distance on either side of the kink zone to assure full protection of the pulmonary artery during a beating heart surgical procedure. The pulmonary artery stent also comprises a handle for inserting and withdrawing the stent through an appropriate incision. Typically the stent will further comprise a guide wire/balloon for placement of the stent in the proper position in the pulmonary artery. In some patients the pulmonary artery stent may be all that is required to protect the left side during a particular beating heart surgical procedure. In other instances the beating heart surgery may require only the pulmonary artery stent and the above tricuspid valve, cannula. In other instances, the use of a pump and cannula system described above may be needed to supplement or augment the right side flow of blood produced by the beating heart during bypass surgery.

This invention further provides the above stent adapted for positioning in other portions of the right side to prevent collapse or restriction in a similar "kink zone" in the vena cava veins, right atrium or right ventricle and to maintain pulmonary blood flow through the right side while the heart is displaced and manipulated during beating heart bypass surgery. As is apparent, the above stent may also be adapted for positioning in the aorta, pulmonary veins, left atrium and/or left ventricle to maintain aortic beating heart blood flow during beating heart bypass surgery.

As is apparent, this invention enables the use of various combinations of the above aspects of this invention to meet the requirements of a particular patient for the successful performance of beating heart or still heart surgery while assuring that the patient's lungs (or lung) provides the oxygenated blood to sustain the patient through the surgery and that a CPB machine and procedure is avoided. Selective use of the above stents, cannulas and/or pump and cannula systems in their various configurations results in minimum invasiveness and minimum contact of the blood with apparatus in or outside the body during beating heart bypass surgery. Thus, this invention enables all beating and still heart surgical procedures without the use of a CPB machine by providing methods and apparatus systems ranging from one or more stents placed to prevent restriction of blood flow produced by the beating heart to pump and cannula systems placed through or around the entire right side and through or around the entire left side to both protect the beating heart blood flow and to augment, supplement or, when necessary, temporarily replace the beating heart blood flow during the surgery.

In preferred embodiments of this invention, the cradle for supporting the beating heart during beating heart bypass surgery can be a flexible film or mesh, or it can be a rigid or semi-rigid member with appropriate openings. The cradle not only provides support for the beating heart in the desired and necessary position for surgical access to heart vessels, it also provides visual access to the appropriate heart vessels on which the bypass surgery is performed.

In another aspect, this invention provides a method for sustaining sufficient blood flow in the patient during heart surgery which comprises:

inserting the cannula portion of a pump and cannula system through the interior of one side of the heart to extend the cannula into the artery or aorta; and adjusting the pump output during the surgery to provide sufficient blood flow in the patient during the surgery. The blood flow referred to in this method can be the pulmonary blood flow through the lungs (or lung) or the circulatory blood flow from the aorta through the body. The cannula and pump system may preferably be placed in and used in both sides of the heart.

In another aspect, this invention provides a method for performing beating heart surgery which comprises:

inserting in the right side of the heart a cannula or stent adapted to protect the blood flow path through the heart when the stented portion of the heart is collapsed or kinked; and performing beating heart bypass surgery while the cannula(s) or stent(s) is in place in the heart. Such cannula or stent may be placed in any portion of or all of the right side of the heart before the surgery is performed. Likewise the cannula(s) or stent(s) may be placed also, or instead, in the left side of the heart before the surgery is performed.

In another aspect, this invention provides a method for performing heart surgery which comprises:

inserting the cannula portion of a pump and cannula system through the tricuspid valve, through the pulmonary valve and a sufficient length into the pulmonary artery to prevent collapse of the right atrium, right ventricle or pulmonary artery when the heart is lifted or displaced during surgery;

pumping blood from upstream of the pulmonary valve into the pulmonary artery whereby the combined flow of blood through the pulmonary artery produced by the beating heart and the pump is sufficient to sustain the patient during surgery; and optionally supporting the beating heart in a cradle to provide surgical access to the lateral or posterior heart vessels.

In another embodiment, this invention provides a system for preventing collapse of the right atrium, right ventricle or pulmonary artery and maintaining blood flow across the pulmonary valve and into the pulmonary artery during heart surgery comprising:

a cannula adapted for insertion through the tricuspid valve, through the pulmonary valve and a sufficient length into the pulmonary artery to prevent collapse of the right atrium, right ventricle or pulmonary artery while the beating heart is lifted or displaced during surgery;

a pump and cannula system adapted for removing blood from the vena cava or the right atrium and transporting the blood through a cannula and into the pulmonary artery; and optionally a cradle for supporting the beating heart while the heart is displaced during surgery and for providing surgical access to lateral or posterior heart vessels. The pump and cannula system can be part of or utilize the cannula adapted for insertion, or can be a separate pump and cannula external of the heart.

In another aspect, this invention provides a method for performing heart surgery which comprises:

connecting a pump intake tube through an incision in the wall of the vena cava or the right atrium to remove blood from the vena cava or the right atrium;

connecting the pump outflow tube into the pulmonary artery through an incision in the wall of the pulmonary artery;

pumping blood from the right atrium through the pump into the pulmonary artery; and optionally supporting the beating heart in a cradle during surgery for surgical access to the heart vessels. When this method is used for still heart surgical procedures, the method further optionally comprises isolating the heart to prevent venus blood flow into the heart and to prevent backflow of arterial blood into the heart during at least a portion of the surgical procedure.

As is apparent, this invention provides and enables various embodiments of methods for beating heart bypass surgery utilizing the various selected combinations of the above described stents, cannulas and pump and cannula systems as appropriate for a particular patient or procedure following the disclosures of this invention and enables heart surgery without the use of CPB machines.

DESCRIPTION OF THE INVENTION

Figure 1:
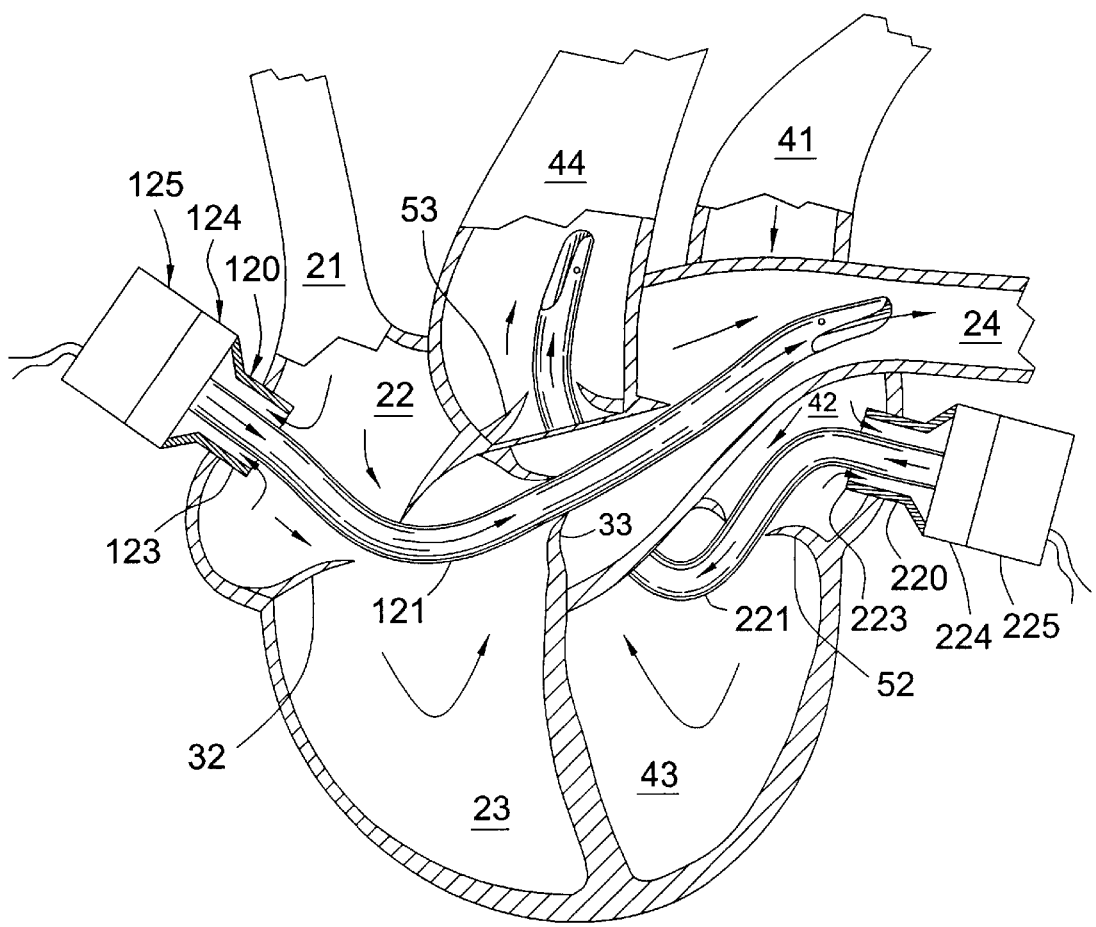
FIG. 1 is a sectional schematic view showing a preferred pump and cannula system according to the invention inserted into the right side including the preferred concentric conduit cannula and reverse flow pump system and showing a separate and optional pump and cannula system inserted in the left side of the heart.

Beating heart bypass surgery has been recognized as desirable because it has the possibility of avoiding the necessity of placing the patient on a full cardio-pulmonary bypass (CPB) system. However, attempts at beating heart bypass surgery have met with limited success and have essentially been limited to surgery on the anterior heart vessels due to problems which develop when the beating heart is lifted or displaced from its normal position in order to perform the beating heart surgery. Typically when the beating heart is lifted or manipulated in order to provide surgical access to posterior heart vessels, a number of difficulties are encountered. When the beating heart is lifted and manipulated, the right side of the heart tends to collapse, particularly the right auricle or atrium and frequently the right ventricle and/or pulmonary artery. When the right side of the heart collapses, pulmonary blood flow either ceases or becomes inadequate, thus forcing the use of CPB. Another difficulty encountered is that, even if the right side of the heart does not collapse, the pulmonary artery and/or the pulmonary vein frequently become crimped or kinked thus also impeding the pulmonary blood flow. Similarly, during the lifting and manipulation of the beating heart for lateral or posterior access, the left side of the heart, particularly the left auricle or left atrium can also collapse or partially collapse, thus impeding aortic circulatory blood flow. Further, when the beating heart is lifted or manipulated for beating heart surgery access or during catheterization or cannulation procedures, the heart may lapse into arrhythmia or disrhythmia or may arrest at least a portion of the time or most of the time that the surgery is being performed thus likewise impeding pulmonary blood flow and arterial circulatory blood flow.

The pump and cannula systems of this invention enable safe heart surgery on anterior lateral and posterior blood vessels, in either beating heart or still heart procedures, without the necessity of using CPB. The systems of this invention provide support for primarily the right side of the heart by internal cannulation in order to prevent the collapse of the right side of the heart and to maintain adequate pulmonary blood flow from the beating heart. Optionally, this invention further provides a system for similar cannulation and support to prevent collapse of the left side of the heart. In addition, the pump and cannula system of this invention provides the pumping of blood through or across the right side of the heart to augment or supplement pulmonary blood flow produced by the beating heart during surgery. With the system of this invention, if the heart temporarily collapses or lapses into arrest or disrhythmia during surgery, the supplemental pulmonary blood flow provided by the pump system of this invention eliminates the necessity of the use of CPB. During beating heart surgery, a temporary collapse or disrhythmia can be corrected to restore the beating of the heart, during which time the pump system of this invention will deliver sufficient supplemental pulmonary blood flow through the lungs to satisfy the patient requirements. Similarly, the pump system of this invention for the left side of the heart can likewise provide sufficient supplemental arterial flow of blood to satisfy the patient requirement until any heart collapse or disrhythmia is corrected during beating heart surgery without the necessity of the use of CPB. As described above, the pump and cannula systems of this invention enable still heart surgery, such as valve or other internal heart repair, without the use of CPB.

In a preferred embodiment of this invention, the pump and cannula system utilize a concentric double-wall cannula, a coaxial cannula, having a short outer conduit forming an annular space around an inner longer conduit where the concentric cannula is connected to a miniaturized reverse flow blood pump. Such a preferred reverse flow pump is disclosed in copending U.S. application Ser. No. 08/933,566 filed Sept. 19, 1997, and PCT Application Serial No. US97/18674 filed Oct. 14, 1997, the disclosures of which are incorporated herein by reference. In this system, the concentric double cannula can be inserted into a single incision, such as in the wall of the right auricle or atrium, the short outer conduit provides intake for the blood entering the reverse flow pump and the outflow of the reverse flow pump feeds into the inner conduit which forms a longer cannula inserted through the tricuspid valve, the pulmonary valve and sufficient length and distance into the pulmonary artery so that the longer cannula provides the internal support to prevent collapse of the right atrium, right ventricle and pulmonary artery. While the preferred concentric double cannula or coaxial cannula is particularly useful with the reverse flow pump, other pumps can be used with such a cannula. Also, a double cannula for intake of blood to the pump and output of blood from the pump can have any desired configuration, such as side-by-side conduits, multi-conduit tubing, in-line intake/output for in-line type pump and others which will be apparent to one skilled in the art. For example, other pumps which can be adapted for use in this invention are disclosed in U.S. Pat. Nos. 4,625,712; 5,376,114 and 5,695,471, the disclosures of which are incorporated herein by reference.

One advantage of this invention is that it allows the beating heart to continue to pump whatever blood it is capable of pumping under the conditions of the beating heart surgery. When the right side is supported according to this invention to prevent collapse of the right side, the beating heart can provide substantial, if not full or sufficient, pulmonary blood flow during the beating heart surgery. The pump and cannula system of this invention provides auxiliary or supplemental pulmonary blood flow through the right side into the pulmonary artery to assure that adequate pulmonary blood flow is maintained at all times during the surgery. The pump, as utilized in the systems of this invention, can be controlled to provide essentially no auxiliary or supplemental blood flow, while the beating heart is providing adequate flow through the supported portion or portions of the right side, or to provide full supporting blood pulmonary flow in the event the output flow of the beating heart decreases or stops.

The pump(s) of the systems of this invention can be controlled in response to conventional parameters, such as oxygen level measured by conventional oximeters, blood pressure measured by conventional means, or other parameters desired to assure proper patient support during and after surgery, such as $CO_2$ level, flow rate, etc. While references relative to this invention are frequently to the "right side", it is to be understood that such disclosure is equally applicable to the left side as well.

Another advantage of the system of this invention is that the concentric cannula in combination with the reverse flow miniature pump, such as disclosed in copending U.S. application Ser. No. 08/933,566, enables the installation of the pump essentially adjacent to the incision where the double cannula is inserted into the right atrium wall or other appropriate location. Thus, the priming volume of the pump and cannula system is minimized to less than about 1,000 ml, preferably less than about 200 ml, more preferably less than about 100 ml and most preferably less than about 50 ml. In this context, "priming volume" refers to the volume of the pump and cannula which is external of the patient and does not include the volume of the portions of the cannulas which are inserted into the patient and thus are immersed in the blood flow. It is especially preferred that the pump and cannula system priming volume be very small, typically less than 30 ml., preferably less than 20 ml., and most preferably less than about 10 ml. The advantages of the very small priming volume will be apparent to one skilled in the art.

Another advantage provided by the pump and cannula system of this invention is that by having the capability of placing the small priming volume pump, including its drive motor, adjacent to or very near the incision, the distance the blood must travel outside the body is minimized, the contact of the blood with tubing, pump components and other apparatus is minimized, and the pump can operate essentially at body temperature, thus eliminating the necessity of cooling or warming the blood, particularly because the blood is outside the body a very short distance and for a very short time. With this system the entire pump and cannula system can be positioned near the chest cavity, within the chest cavity itself, near or adjacent to the heart, or can be positioned in the support cradle near or adjacent the heart to obtain the minimum possible pumped blood flow path. Other advantages will be apparent to one skilled in the art, including the fact that with the entire pump, drive motor and cannula system miniaturized and configured to be contained in the chest cavity or in the support cradle with the heart, this system eliminates the disadvantages of having numerous tubes, cables, etc., from the patient's chest cavity to external equipment. Even in the preferred embodiment of the present invention, where the pump and cannula system is installed in or across the right side of the heart, and a separate pump and cannula system is installed or across in the left side of the heart, the only lines extending from this system to external equipment is a single cable from each pump to the external power supply for providing power to each pump. This single cable can contain electrical connection for supplying electrical power to the pump motor near the heart or can be a flexible drive cable to transmit power to the pump from a remote motor. Thus, the pump and cannula system of this invention provides the surgeon much better surgical access to the heart and visibility of the heart by eliminating the CPB tubing and other associated cables and pumps which are conventionally used in bypass and other cardiac surgical procedures.

The pump and cannula system of this invention can best be understood by reference to the illustration in FIG. 1, which shows the pump and cannula system of this invention in place in the right side of the heart for pulmonary blood flow and in the left side of the heart for arterial blood flow. Referring to the drawing, the blood flow in right side of the heart enters from vena cava 21 through the right auricle or atrium 22 through tricuspid valve 32 into the right ventricle 23. From there, the blood passes through the pulmonary valve 33 into the pulmonary artery 24. The preferred pump and cannula system of this invention is adapted for use in the right side by insertion through a single incision in the wall of right atrium 22 as illustrated or an incision in vena cava 21 or ventricle 23. The concentric cannula 120 is inserted into the incision where the outer conduit 123 seals with the wall of right atrium 22 at the incision. The outer conduit 123 provides the annular space between outer conduit 123 and inner conduit 121 for the inflow of blood to pump 124, which is driven by motor 125. The longer inner tube or cannula 121 is inserted through tricuspid valve 32, pulmonary valve 33 and into pulmonary artery 24. Insertion of cannula or tube 121 through the heart and into the pulmonary artery may be accomplished in any conventional method, such as the optional use of a balloon guidewire. The length into which cannula 121 extends past pulmonary valve 33 into pulmonary artery 24 will depend on the beating heart bypass surgery procedures performed and on other factors. However, it is important that cannula 121 extend through and past the kink zone, which will vary in size and location depending on condition of the patient, the surgical procedure performed and the extent of movement and manipulation of the heart during surgery. The kink zone will frequently extend up to the point where the pulmonary artery is not moved during surgery. It is generally expected that cannula 121 will need to extend up to about 15 cm beyond pulmonary valve 33 and into pulmonary artery 24. Such a length is generally sufficient to prevent kinking or collapsing of pulmonary artery 24 during the positioning of the heart for beating heart bypass surgery. Preferably the length beyond pulmonary valve 33 will generally be up to about 10 cm, or preferably up to about 7 cm, or about 4 cm but may be as little as about 1 cm depending on the kind of cannula used. As can be seen in the illustration of FIG. 1, the system of this invention enables the heart to continue pumping blood in its normal fashion to provide pulmonary blood flow around cannula 121, to the extent that the heart is capable, during the lifting and manipulation of the heart during surgery. A cannula and pump system according to this invention assures a supplemented or augmented flow of blood to the pulmonary artery 24, even in the event of decreased output of the heart or in the event of a disrhythmia or other interruption of pulmonary blood flow by the beating heart. Under normal circumstances and at most times during the beating heart surgery, the internal support provided by cannula 121 will prevent the collapse of the right side of the heart and enable the heart to continue pumping at least a portion of its normal blood output into pulmonary artery 24. The combined flow of the blood flow produced by the beating heart and the blood flow produced by pump 24 through cannula 121 is at all times sufficient to sustain adequate pulmonary blood flow to sustain the patient during surgery. In the event of a disrhythmia, the pump 124 can be increased in output to compensate until the disrhythmia is corrected.

While FIG. 1 illustrates a preferred pump configuration, it is apparent any suitable pump design or configuration can be used in this invention. For example, pump 124 may be placed inside atrium 22, in which case outer conduit 123 would be eliminated. Also, motor 125 can be integral with pump 124, as shown, or can be a remote motor connected to the pump by a sheathed drive cable. When a pump is used where the entire pump is placed within the atrium or other part of the blood system, the pump is essentially a zero priming volume pump and cannula system because no blood volume is taken outside the heart or blood vessels.

Further illustration in FIG. 1, the optional left side pump and cannula system can also be used to prevent collapse of the left side of the heart as well as protect arterial blood flow during beating heart surgery. As with the right side, concentric cannula tube 220 is inserted into an incision in the wall of the left atrium 42 and sealed with the wall at the incision. The longer inner tube or cannula 221 is inserted through the bicuspid or mitral valve 52 and through the aortic valve 53 and extended into the aorta 44. As with the above description for the right side, the blood flow from the pulmonary vein 41 enters left atrium 42 and is normally pumped through the left ventricle 43 into aorta 44. With the pump and cannula system of this invention, a portion or all of the blood enters pump 224 through the annular space between outer cannula 223 and inner cannula 221 and is pumped through the inner cannula 221 into the aorta 44 to assure the maintenance of adequate aortic blood flow during beating heart surgery.

As will be apparent to one skilled in the art, the above description of the double wall concentric cannula and reverse flow blood pump having a minimum priming volume constitute preferred embodiments of the present invention, but other pump and cannula configurations and designs may be employed in the pump and cannula systems of this invention. For example, a cannula may be inserted into the wall of vena cava 21 or the wall of atrium 22 to draw blood into an in-line pump which can then return the blood through cannula 121 positioned as shown in FIG. 1. Thus, various conventional blood pumps can be used in such configuration in accordance with the pump and cannula systems of this invention even those of large priming volume provided that cannula 121 extending into pulmonary artery 24 extends through the kink zone as disclosed herein.

Another example of an embodiment of the pump and cannula system of this invention includes a cannula which may be inserted through vena cava 21 either through an incision through the wall of vena cava 21 or through an incision in a femoral vein leading to vena cava 21, where such a cannula contains an in-line pump, for example, as disclosed in U.S. Pat. No. 4,969,865, the disclosure of which is incorporated herein by reference, provided that the output of the pump is fed into cannula 121 positioned through the kink zone of pulmonary artery 24 in accordance with this invention. As is also apparent from the above description and the illustration in FIG. 1, the alternative pump and cannula embodiments of this invention are equally applicable to the left side of the heart for support of the left side during beating heart bypass surgery.

Figure 4:
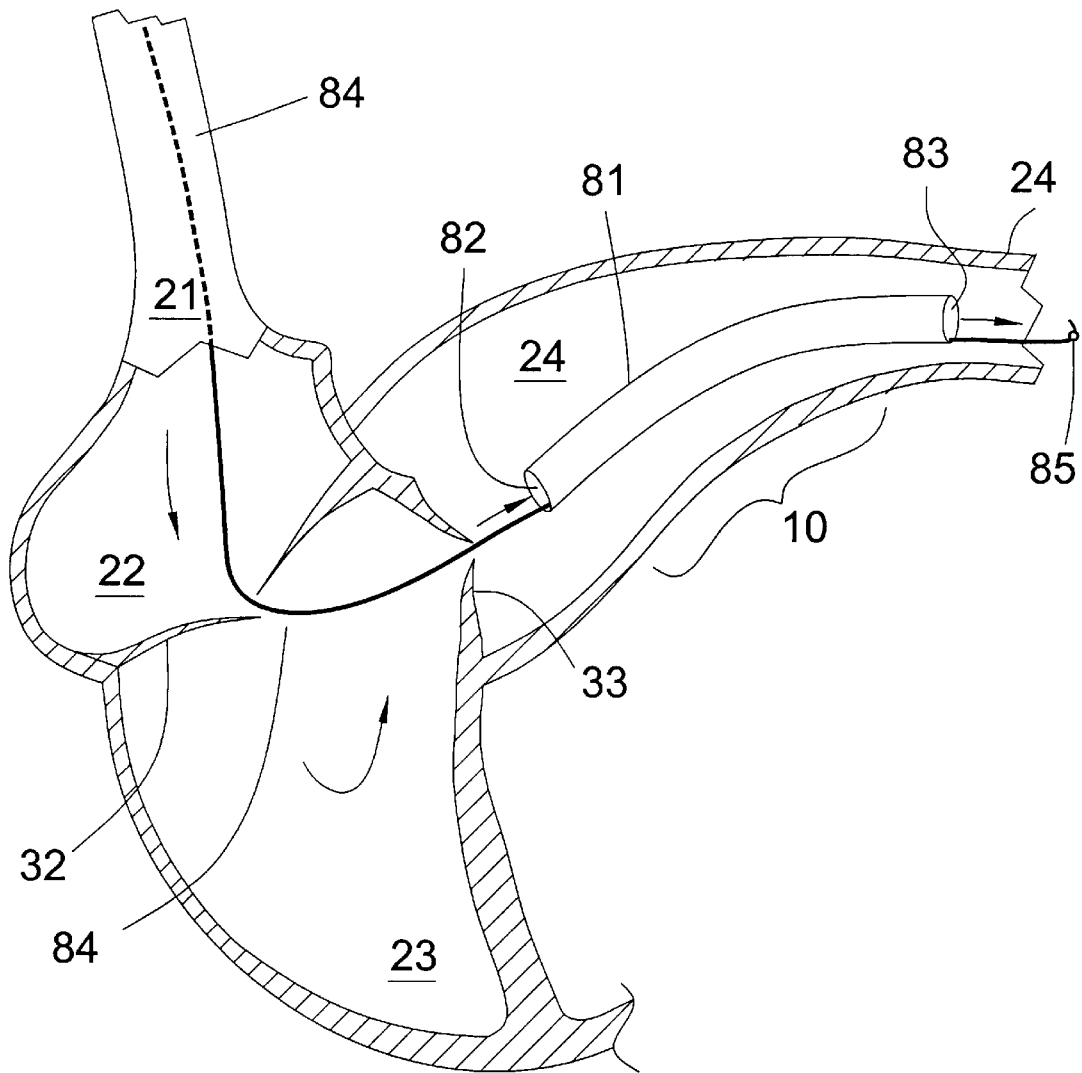
FIG. 4 is a sectional schematic view of the right side showing an example of the stent of this invention and the use thereof.

In another embodiment of this invention cannula 121 may be positioned so that it extends only into ventricle 23 so that the output of the pump is into ventricle 23. This enables the pump to be used to fill or preload the ventricle with blood, then allow the ventricle to pump the blood on through the pulmonary valve and pulmonary artery. The ventricle is sometimes capable of pumping blood out but not capable of drawing blood in when it is in a stressed or distorted condition during surgery. In this embodiment of the invention the pump and cannula system is positioned to assist the ventricle, without the necessity of placing the cannula through the pulmonary valve and pulmonary artery. The left side can be assisted with a similar pump and cannula positioned for prefilling the left ventricle. This embodiment of the invention can further comprise a stent as illustrated in FIG. 4.

It is to be understood that the pump and cannula system illustrated in FIG. 1 enables still heart surgical procedures to be performed without the use of CPB. The pump and cannula systems of this invention provide sufficient and sustained pulmonary blood flow and circulatory blood flow during surgery in a highly controllable manner to assure the patient's lungs (or lung) provides adequate oxygenated blood even during still heart surgery or surgery where the heart is isolated from body blood flow.

Figure 2:
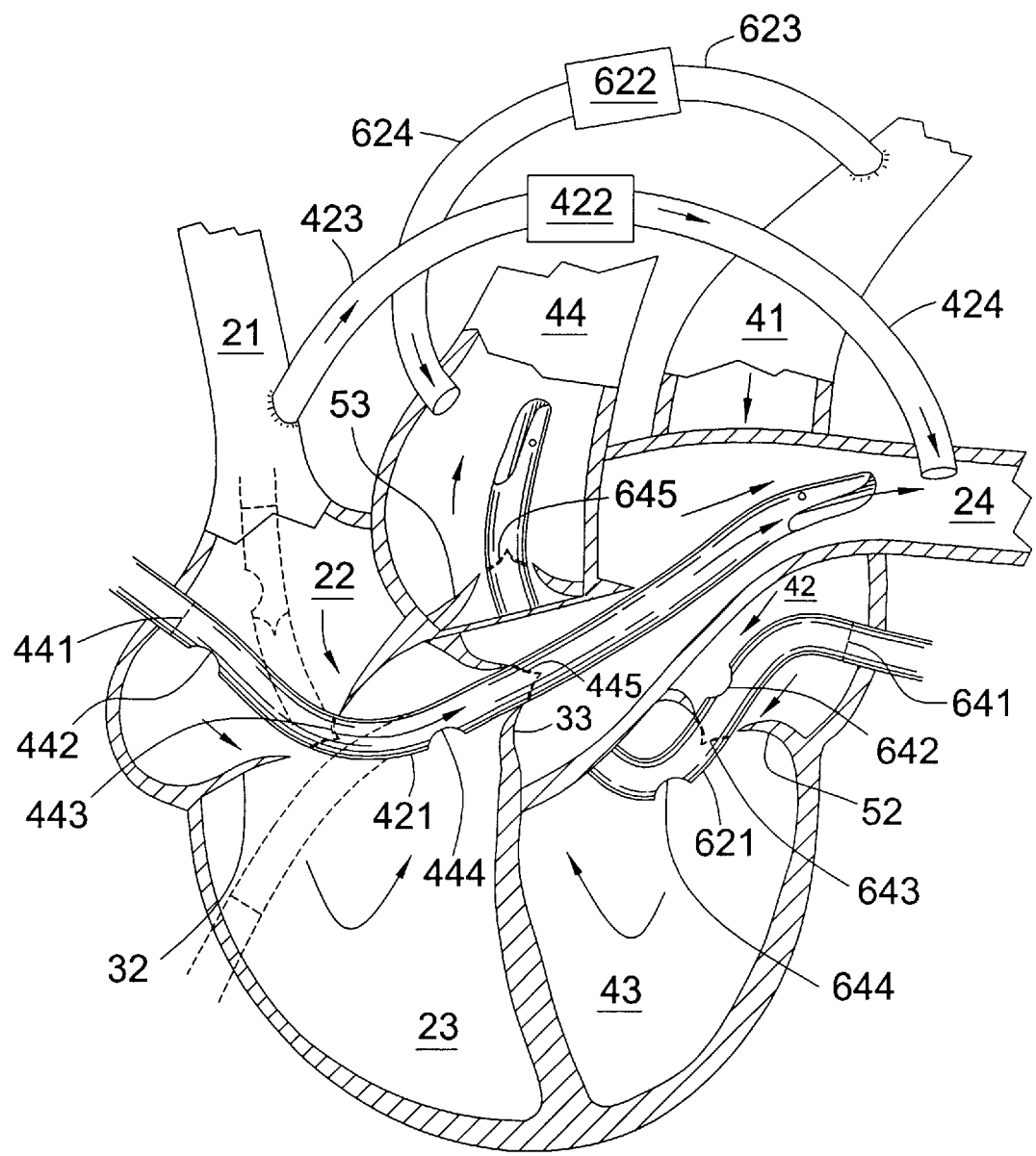
FIG. 2 illustrates an embodiment of the invention where the cannula is inserted in the left side of the heart to prevent collapse and the pump system transports blood from the right atrium to the pulmonary artery external of the heart and illustrates a similar optional embodiment for the left side of the heart.

An alternate aspect of this invention, as illustrated in FIG. 2, can be used with various types of blood pumps, although a minimum priming volume pump is preferred in most applications of the various embodiments of this invention. Referring to FIG. 2 illustrating the various embodiments of this aspect of the invention, support cannula 421 is inserted through tricuspid valve 32 and pulmonary valve 33 and extended into pulmonary artery 24 a sufficient distance to extend through the kink zone of pulmonary artery 24. It will be recognized that while FIG. 2 illustrates cannula 421 as inserted through an incision in the wall of atrium 22, cannula 421 may also be inserted through vena cava 21 from an incision in another part of the body such as a femoral vein or jugular vein or other desired access point. While cannula 421 is referred to as a "cannula", it will be recognized in this aspect of the invention and the various embodiments thereof that member 421 may or may not function as an actual cannula, i.e., for withdrawing or inserting fluids from an into the body. Member 421 may actually be a solid, flexible rod or a closed tube which provides support for preventing the collapse of the right side, vena cava 21, atrium 22 and pulmonary artery 24, thereby providing a support structure around which the beating heart can continue to pump blood even though a portion of the right side walls may have folded or collapsed against a portion of the surface of member 421. Alternatively, member 421 may contain opening 444 in a hollow tube portion upstream of pulmonary valve 33 whereby blood may enter the tube upstream of valve 33 and exit the tube at opening 444 in ventricle 23 or at the end of tube 421 in pulmonary artery 24. In this configuration, the tube would need to be blocked in the vicinity of pulmonary valve 33 and upstream of opening 444 in order to prevent back flow through the tube.

In another similar embodiment, member or tube 421 may be constructed to contain opening 442 in the area of atrium 22 to allow blood to enter and flow through the interior of tube 421. In such an embodiment, member 421 would require blocking element 441 to prevent back flow of blood. Opening 442 in the area of atrium 22, check valve 443 opening 444 in the area of ventricle 23, and check valve 445 provide a protected path for beating heart blood flow. In such a configuration, the beating heart would be enabled to withdraw blood through tube 421 from vena cava 21 or atrium 22 into ventricle 23 and expel blood from ventricle 23 through check valve 445 into pulmonary artery 24. As will be appreciated in these embodiments of the invention, member 421 may be a solid member where the beating heart blood flow is around the exterior of the support member 421 which functions to prevent the collapse or kinking of the various portions of the right side. Member 421 can contain either opening 444 and check valve 445, or opening 442 and check valve 443, or both openings and both check valves, of course, with seal or block 441, so that the blood flow from the beating heart can flow through the inside of support member 421 as well as around the outside of member 421.

Tube member 421 can also be inserted into the heart through an incision in the wall of the right atrium 22 or through the wall of the right ventricle 23, as depicted in FIG. 2 by dashed lines. In latter case where member 421 would only extend through ventricle 23 into pulmonary artery 24 only one check valve 445 and opening 444 would be needed (valve 443 and opening 442 would be unnecessary).

As will be apparent to one skilled in the art the above system described in detail for the right side is equally applicable according to the present invention to the left side. As illustrated in FIG. 2, member 621 can be inserted through left atrium 42, through bicuspid valve 52 through left ventricle 43 through bicuspid valve 52 and into aorta 44 and extending through the kink zone of aorta 44. As explained above with respect to the right side, member 621 may be a solid member which provides support for the left side and provides for beating heart blood flow around the outside of support member 621. Alternatively, member 621 may be a tube or cannula adapted to also provide beating heart blood flow through the interior of member 621 as well as the exterior. In such embodiments, cannula 621 will contain check valve 645 and opening 644 with blocking member 641 enabling the left ventricle 43 to pump blood through the interior of cannula 621 into aorta 44 past the aorta kink zone. Alternatively, cannula 621 can contain check valve 643 and opening 642 with blocking member 641 to enable beating heart blood flow from atrium 42 into ventricle 43 through the inside of cannula 621. In a preferred embodiment, cannula 621 will contain both check valve 643 and 645 and both openings 642 and 644 to enable the best protected beating heart blood flow from pulmonary vein 41 through the left side and into aorta 44 past the kink zone. It will also be apparent that member 621, depending on configuration, can be inserted as shown through the wall of atrium 42 or can be inserted through an incision in pulmonary vein 41 or through the wall of ventricle 43, depending on the desired configuration.

A similar configuration can be used in the left side of the heart in the form of tube or rod member 621 which can be a solid support member inserted through the wall of atrium 42 through the bicuspid valve 52 through the aortic valve 53 and into aorta 44 in order to provide physical support for the left side to prevent collapse or kinking of the left side and to provide for beating heart blood flow around the outside of support member 621 during beating heart surgery. Alternatively, member 621 may be a tubing member adapted to provide beating heart.blood flow through the tube. In this configuration, tube member 621 will contain a block 641 to prevent flow of blood back into the tube, opening 642 for inlet of blood, check valve 643 to prevent back flow of blood when ventricle 43 contracts, opening 644 for blood flow into and out of ventricle 43, and check valve 645 to prevent back flow of blood into ventricle 43 when ventricle 43 expands. In this configuration, member 621 not only supports the left side and prevents collapse or kinking of the left side, it facilitates beating heart blood flow both around the outside of member 621 and through the inside of member 621 to assure the maximum beating heart blood flow into aorta 44 during beating heart surgery. In addition to the access of member 621 being inserted through an incision in the wall of atrium 42 as shown in FIG. 2, member 621 can also be inserted through pulmonary vein 41 or through an incision in the wall of ventricle 43, which alternative insertion points are not shown in FIG. 2. As will be apparent if member 621 is a hollow tube and is inserted through the wall of ventricle 43, then opening 644 and check valve 645 will be necessary and check valve 643 and opening 642 will be unnecessary.

FIG. 2 further illustrates another aspect of the invention, wherein pump and cannula system is utilized to supplement or replace the beating heart blood flow. This aspect is illustrated in FIG. 2 together with the above described support systems, but it is to be understood that the illustrated pump and cannula systems positioned external of the heart can be employed separately from and without the use or presence of the above described support systems. This aspect of the pump and cannula system of this invention is accomplished by inserting cannula 423 into an incision in vena cava 21 or in an incision in the wall of atrium 22 for drawing blood to pump 422. The blood is then passed by pump 422 through cannula 424 into pulmonary artery 24 through an incision in the wall of pulmonary artery 24. As disclosed above, the control of pump 422 can be regulated depending on oxygen level, blood pressure at a particular point or general blood pressure, etc., in order to either supplement and augment the pulmonary blood flow produced by the beating heart around and/or through support member 421 or provide substitute pulmonary blood flow during those periods, if any, when the right side of the heart experiences an arrest or other temporary blockage during the beating heart surgery. Of course, in still heart procedures, it will be controlled to provide the entire necessary pulmonary blood flow.

The left side support system for providing circulatory blood flow through the aorta is provided by a pump and cannula system which comprises cannula 623 inserted into the pulmonary vein 41 to direct blood from the pulmonary vein to pump 622. The pump then returns the blood to aorta 44 through cannula 624 inserted through an incision in the wall of aorta 44. As indicated above with respect to the right side, the pump and cannula system 622, 623 and 624 can be operated to supplement the beating heart blood flow in the left side during beating heart surgery or can provide the entire necessary circulatory blood flow during still heart surgical procedures. The output of pump 622 may be minimum when the beating heart blood flow through the left side is strong and can be maximized when the left side experiences an arrest or a kink or obstruction or is stopped for still heart surgery. The control of pump 622 may be controlled in relation to aortic blood pressure or other desired control parameters as discussed above.

In the above aspect of this invention it is important to note that the pump and cannula systems for the right side and left side should be positioned such that the intake cannulas 423 and 623 can be inserted through an incision at any point where it is desired to withdraw the blood, but it is preferred that they be inserted at a point upstream of where any collapse, obstruction or kink may occur during the beating heart surgery. Similarly, the output cannulas 424 and 624 may be inserted to return the blood to any point desired, but it is preferred that the return cannulas be positioned downstream of where any collapse, obstruction or kink may occur during the beating heart surgery. As disclosed above, it may be desired during still heart procedures to provide isolating blocks, balloons, clamps, etc. to prevent unwanted venus blood flow into the heart and/or prevent unwanted backflow of arterial blood into the heart. For example, cannula balloon collars as illustrated in FIGS. 15 and 18 of application Ser. No. 08/933,566, incorporated herein by reference, would be suitable for such isolation of the heart where desired.

Figure 3:
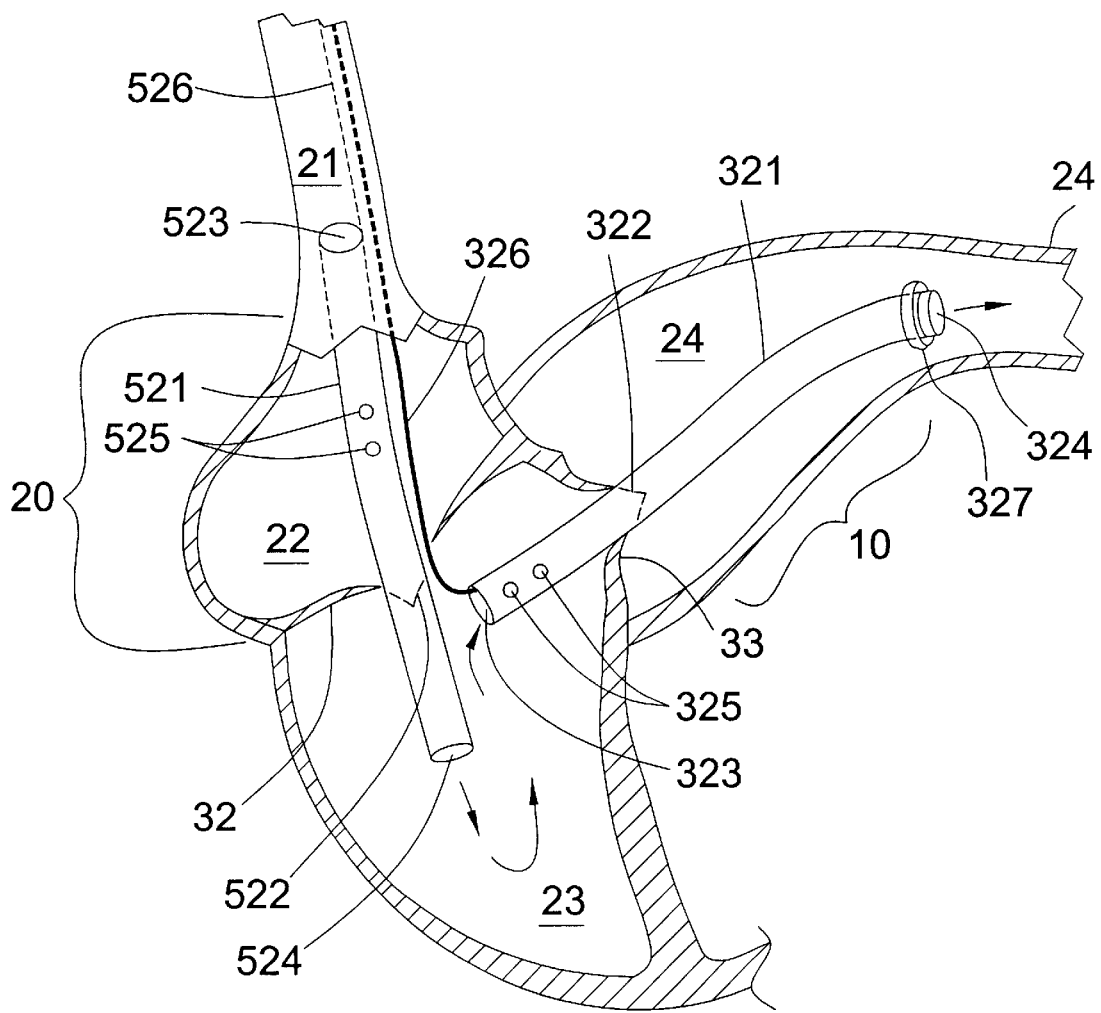
FIG. 3 is a sectional schematic view of the right side showing valved cannulas and the use thereof according to this invention.

In the pump and cannula systems of this invention, a preferred device for and method of control of the pump speed and output is to include a pressure transducer at the arterial blood flow area, preferably as part of the discharge ends of cannulas 121 and 221 in FIG. 1 and 424 and 624 in FIG. 2, to measure pulmonary artery blood pressure and aorta blood pressure. This blood pressure measurement can provide the basis for a manual or automatic control of the individual and separate pump speeds and outputs. The desired or target pulmonary and aortic blood pressures can be determined by the surgical team for each patient depending on condition of the patient and surgical procedure being performed. The desired or target pressures may change or be different for different stages of the surgical procedure. In general, a desired pressure range is about 20–30 mmHg, although pressures as low as about 10–15 mmHg may be acceptable for limited periods of time. It is further preferred that the control system incorporate other input data, in addition to arterial pressure, such as blood pressure elsewhere in the body, blood oxygen level, actual blood flow volume, blood $CO_2$ level, etc. A desired automatic control criteria is where a control loop for each pump is established whereby a target total blood flow is maintained by the sum of any beating heart blood flow output plus the pump flow output. Thus, the patient is assured of adequate pulmonary and circulatory blood flow throughout the surgery regardless of the output of the heart, without any CPB machine use. The pulmonary artery pressure and pulmonary blood flow rates will need to be adjusted accordingly when only one lung is being used during the surgery, and the aortic circulatory blood flow may also have to be adjusted in such mode of operation. Reference to FIG. 3 illustrates another aspect of this invention and exemplifies preferred embodiments of this aspect. FIG. 3 depicts the right side portion of the heart including vena cava 21 and pulmonary artery 24. In this illustration, two zones are identified relative to the systems and methods of this invention. The first is the zone referred to as a "kink zone" 10 which is the portion of the pulmonary artery which tends to fold, kink or otherwise become constricted when the beating heart is lifted and manipulated during beating heart bypass surgery in order for the surgeon to gain surgical and visual access to the lateral and posterior vessels of the heart. The length and actual area of the actual kink zone may vary from patient to patient and vary depending on the bypass procedure being performed and the extent to which the heart is moved and manipulated. However, the kink zone will be apparent to one skilled in the art and in general will be the area of the pulmonary artery extending about 15 cm from the pulmonary valve 33. In this embodiment of the invention pulmonary cannula 321 is adapted to be positioned with opening 323 in the right ventricle 23 and the length of cannula 321 extends through pulmonary valve 33 and into pulmonary artery 24 so that outlet 324 is downstream of kink zone 10. Cannula 321 further comprises check valve 322 adapted to allow blood to flow through cannula 321 when the right ventricle 23 contracts and prevent back flow of blood through cannula 321 when right ventricle 23 expands and further compresses handle 326 adapted for inserting the cannula into proper position and maintaining cannula 321 in the proper position during the beating heart bypass surgery procedure. As illustrated in FIG. 3 cannula 321 can be inserted with handle 326 through the vena cava 21 through an incision in the wall of the vena cava or an incision in a remote vein such as the femoral vein or jugular vein. Alternatively, cannula 321 may be inserted through an incision in the wall of the right atrium or through an incision in the wall of the right atrium or through an incision in the wall of the right ventricle. However, the remote access incision is preferred in order to keep the heart relatively free of encumbrances and other incisions to enhance the access for beating heart bypass surgery. With cannula 321 in position, the beating heart blood flow can be maintained both around the outside of cannula 321 when pulmonary valve 33 opens around the outside of cannula 321 and through the interior of cannula 321 when there is any constriction which prevents the blood flow around the outside of cannula 321. Check valve 322 may be positioned at any appropriate location along cannula 321 and is adapted to prevent back flow of blood through cannula 321. As mentioned above, the particular type of valve suitable for use may be selected for one skilled in the art. In a preferred embodiment, the cannula 321 may include a balloon tip at or near the outlet end 324 in order to aid in the insertion and proper positioning of cannula 321. While cannula 321 is in position, the heart may be lifted and manipulated and the beating blood flow through the kink zone will be protected and maintained by cannula 321.

In another embodiment of the aspect of this invention illustrated in FIG. 3 involves the recognition that when the beating heart is lifted and manipulated for beating heart bypass surgery, the right atrium 22 and adjacent areas of the vena cava tend to collapse and restrict the blood flow. This area is identified in FIG. 3 as collapse zone 20. This invention provides atrium cannula 521 adapted to have an inlet 523 position upstream of the collapse zone 20 and an outlet end positioned in right ventricle 23. Cannula 521 further comprises check valve 522 adapted to prevent back flow of blood when the right ventricle 23 contracts and handle 526 adapted for inserting cannula 521 into proper position and maintaining cannula 521 in proper position during beating heart bypass surgery procedure. Optionally, cannula 521 can also include additional inlet openings 525 positioned as appropriate along the length of the cannula upstream of valve 522. Cannula 521 is adapted to allow beating heart blood flow around the outside of the cannula when tricuspid valve 32 opens for blood to flow into the right ventricle 23. In addition, the cannula 521 is adapted to provide blood flow through the interior of the cannula when there is a collapse or restriction of the beating heart blood flow around the outside of the cannula. Thus, beating heart blood flow is protected and maintained during beating heart bypass surgical procedures, even when lifting or manipulating the heart causes a partial or complete collapse of the right atrium 22 or other portion of collapse zone 20.

Cannula 521 can be inserted through the same incisions as mentioned above through which cannula 321 is inserted. However, it is preferred that the cannula 521 be inserted through the vena cava from a remote incision such as a femoral vein or jugular vein for the same reasons mentioned above.

In another embodiment of this aspect of the invention, cannulas 321 and 521 can be connected together an operated as a single cannula or can be manufactured as a single continuous cannula having the appropriate openings and check valves as illustrated in FIG. 3 so that a single cannula can provide protection of collapse zone and protection of kink zone 10. An advantage of such a configuration would be that the cannula can be inserted through a single incision with a single guidewire or balloon for guidance and a single handle for positioning and holding the cannula in proper position during surgery. In another embodiment, cannula 321 and cannula 521 can be sized so that one will nest or telescope inside the other for insertion. For example, cannula 521 can be made slightly smaller diameter so that it will nest inside cannula 321 during insertion. In this fashion the two cannulas can be inserted through a single incision and the guidewire/balloon at the outlet end 324 of cannula 321 will guide both cannulas into proper position. Each cannula would have its separate handle for positioning and holding the cannula in position during surgery. In such embodiment, the nested cannulas would be inserted through the appropriate incision and when cannula 521 reached its proper position at the collapse zone and the tricuspid valve handle 526 can then hold cannula 521 in its proper position while cannula 321 can continue on its path of insertion until it is properly positioned across the pulmonary valve and the kink zone. Also, in such embodiment, the inner cannula can have one lumen for blood flow and containing the check valve and a second lumen for the handle of the outer cannula. Other configurations and embodiments of the cannula system illustrated in FIG. 3 will be apparent to one skilled in the art.

While only the right side of the heart is illustrated in FIG. 3, it will be equally apparent to one skilled in the art that the same system can be readily adapted for the left side of the heart for protection of the left atrium from collapse and protection of the aorta from kink or restriction during beating heart bypass surgery.

Another aspect of this invention is illustrated in the embodiment shown in FIG. 4. As illustrated in FIG. 4, this invention provides a stent member 81 having an inlet 82 and an outlet 83 wherein the stent is sufficient length and adapted to be positioned in the pulmonary artery 24 over the length of kink zone 10. In this aspect of the invention, stent 81 is of sufficient size, strength and flexibility to provide protection against the pulmonary artery 24 becoming folded, kinked or otherwise obstructed when the heart is lifted and manipulated during beating heart bypass surgery for surgical access to the lateral or posterior vessels of the heart. Stent 81 may be sized to approximate the size of the pulmonary artery in which it is placed so that essentially all of the beating heart blood flow passes through the interior of the stent 81 with a minimum amount, if any, of blood flow around the outside of the stent. Stent 81 also comprises handle 84 which is used for inserting the stent through an appropriate incision, for holding the stent in proper position during the beating heart bypass surgery and for withdrawing the stent. Typically, stent 81 will also comprise an optional guidewire/balloon portion 85 adapted for facilitating the guidance of stent 81 through vena cava 21 and the heart chambers and valves as well as other blood vessels in order to properly position stent 81 and across the kink zone 10 of pulmonary artery 24. In some patients undergoing beating bypass surgery, stent 81 inserted to protect the pulmonary artery from blood flow restriction, may be all that is required to assure that the beating heart blood flow is maintained during the beating heart bypass surgery. However, in other patients and depending on the surgical procedure to be performed other protection devices of this invention may be used in combination with stent 81. For example, it may be desirable to protect the right atrium from collapse by also using cannula 521 as illustrated in FIG. 3, which can be inserted separately after stent 81 is inserted and properly placed or cannula 521 can be nested or telescoped with stent 81 so that they are inserted at the same time through the same incision, then separated at the time that they reach tricuspid valve 32 whereby the cannula 521 is retained in proper position across the collapse zone 20 and stent 81 is allowed to continue through ventricle 23 and pulmonary valve 33 to be positioned in kink zone 10 or pulmonary artery 24. In another embodiment of this invention, instead of using cannula 521 in combination with stent 81, a second stent 81 can be used in addition to the first stent 81 and positioned across collapse zone 20 of vena cava 21 and atrium 22, wherein the stent is positioned close to tricuspid valve 32, but not extending through bicuspid valve 32. Such embodiment employing two stents 81, one positioned in collapse zone 20 and one positioned in kink zone 10, may provide sufficient protection in some patients for the beating heart blood flow during lifting and manipulation of the heart during beating heart bypass surgery.

As will be apparent, other combinations of the various embodiments of the present invention can be used as appropriate for a particular patient. For example, stent 81 may be positioned in kink zone 10 and used in combination with a pump and cannula system 124, 120 and 121 as shown in FIG. 1, except that inner tube or cannula 121 would be modified to extend only into ventricle 23 and not through pulmonary valve 33. In such a combination, the pulmonary blood flow from vena cava 21 and atrium 22 would not only be protected, but could be augmented and supplemented by pump 124, by pumping blood from atrium 22 into ventricle 23. As also will be apparent to one skilled in the art utilizing the disclosure of the present invention, stent 81 can also be utilized for insertion into aorta 44 across the kink zone of aorta 44 and/or into the collapse zone of pulmonary vein 41 and atrium 42 to protect the beating heart blood flow in the left side in a similar fashion as illustrated in FIG. 4 showing the right side.

As will be recognized by one skilled in the art, the above discussed cannulas, stents, tubing and the like will obviously be made of appropriate flexible bio-compatible materials which have sufficient flexibility, radial stiffness and other strength properties appropriate to the function intended in this invention. In most applications the cannulas and stents utilized in this invention must have appropriate radial strength and stiffness to resist collapsing or kinking under the stresses and compressive loads imposed on them when inserted in the appropriate blood vessels and the heart lifted and manipulated during beating heart bypass surgery. In some instances, soft and flexible materials such as silicones may be desirable and may need to be reinforced with wire or other material to provide the radial stiffness and resistance to collapsing necessary to be useful in the present invention.

In another aspect this invention provides apparatus and methods for placement and positioning of the stents and cannulas of this invention. In this aspect, a pressure transducer is provided on the end of the cannula or stent for detection of the blood pressure patterns present at the end of the cannula or stent. Since the pressure patterns are different and distinct in different parts of the system, the pressure transducer is used to determine whether the end of the cannula or stent is in the vein, atrium, ventricle or artery. The pressure transducer on the end of the cannula or stent enables precise placement at the desired location. Multiple transducers may be used along the length of the cannula or stent or at both ends thereof to provide the information needed for precise placement of the cannula or stent. For example, side ports along the cannula with separate lumens for the transducer connecting wire can be used to provide desired information for monitoring the condition of the patient, such information is also useful in controlling the pumps in the pump and cannula system employed according to this invention.

Figure 5:
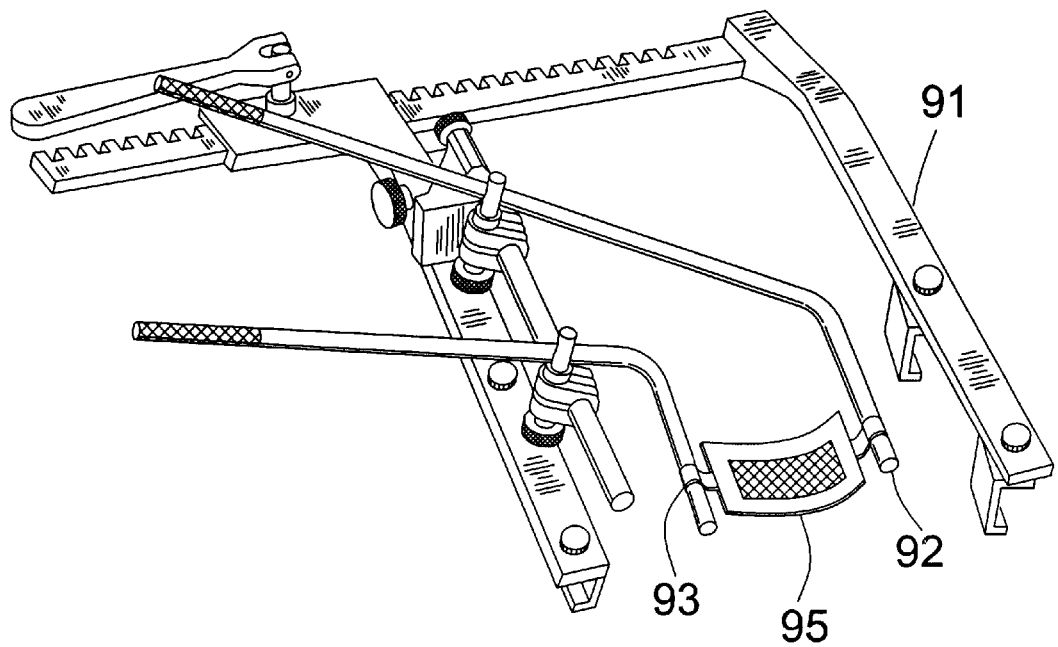
FIGS. 5 and 6 are illustrations of the beating heart surgical cradle of this invention.

The cradle for use in supporting the heart is illustrated in FIG. 5 and may be made of any suitable material and structure. A mesh structure provides flexibility, while a film or solid structure provides other advantages. The material may be any bio-compatible material which is sufficiently flexible and smooth to support the beating heart without causing damage or abrasion to the exterior of the beating heart. A mesh or film can provide appropriate support while also providing the surgeon unlimited access to the various surface areas of the beating heart. The mesh or film material used should be a rip-stop type structure or material so that the surgeon may cut away part of the cradle for surgical access to a portion of the surface of the beating heart and the mesh or film used for the cradle will not split or run to form an opening any larger than the opening cut by the surgeon. The mesh type of cradle structure can be a plastic molded screen of any appropriate grid size and design having openings in the grid ranging from one to about 30 mm with the grid strands themselves ranging in width and/or thickness from several mils to 1 mm or more. The mesh structure useful as a cradle in this invention can also be woven or braided from bio-compatible fibers. A braided structure in particular will tend to flex with the surface of the beating heart without abrading the surface of the heart.

FIG. 5 is a perspective view of one embodiment of the use of the cradle according to the present invention. In this embodiment, a sternum spreader 91 is fitted with adjustable attachments 92 and 93 adapted for supporting a cradle according to the present invention which in turn is adapted for supporting the beating heart in a lifted or rotated position to enable access for beating heart bypass surgery. Cradle 95 is adapted for attachments at the ends thereof to support members 92 and 93, whereby the cradle attachment to the supports is adjustable with respect to height and position and the support members 92 and 93 are likewise adjustable in height and position, thereby providing the surgeon full flexibility with respect to positioning the heart as needed for surgical access to the heart vessels. Other configurations and other supports for the cradle will be apparent to one skilled in the art. Other embodiments of the cradle will likewise be apparent to one skilled in the art in order to fulfill particular needs in terms of positioning the beating heart as needed by the surgeon. In some instances, the heart may only need to be lifted, but in other instances the heart may need to be lifted and rotated. The selection of the cradle structure materials and design in combination with the cradle support will be apparent to one skilled in the art following the disclosure set forth herein.

Figure 6:
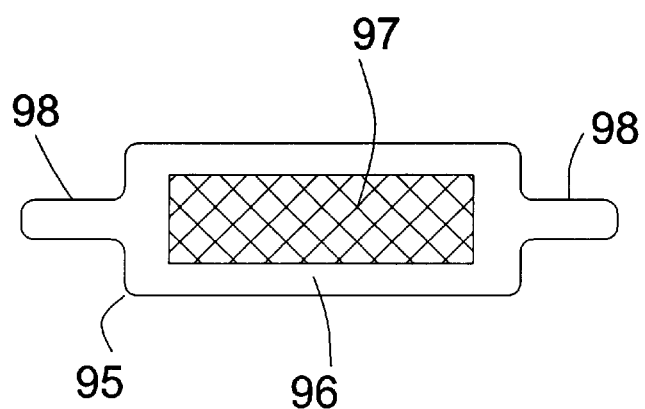

FIG. 6 is an illustration of an example of the cradle which is formed of a flexible plastic framework 96 in combination with an interior portion of a flexible mesh 97 for supporting the beating heart. The ends 98 of the cradle are adapted to engage support members such as 92 and 93 illustrated in FIG. 5.

In utilizing the various aspects and combinations of the present invention, the basic method of the present invention includes the first step of inserting into the patient the selected stents, cannulas and/or pump and cannula systems as appropriate for a particular patient and a particular surgical procedure to be performed. After the appropriate combination of apparatus has been inserted into the patient and particularly into the kink zones and the collapse zones, then the beating heart can be subjected to lifting and manipulation, placement in the cradle, adjustment of the cradle and similar operations without unduly restricting the blood flow. However, if the beating heart blood flow is constricted or temporarily interrupted, or if a still heart surgical procedure is to be performed the pump and cannula systems of this invention will provide supplemental or total pulmonary and/or aortic blood flow during the time that the beating heart blood flow is restricted or interrupted. Accordingly, this invention provides apparatus and systems to enable heart surgery of any desired procedure while using the patient's lungs (or lung) for supplying oxygenated blood and, thus eliminating the use of CPB machines for heart surgery. The pump and cannula systems of this invention, whether internal or external of the heart, can provide 0–100% of the required blood flow to sustain the patient with the heart providing 100–0% of the blood flow. When the pump system is providing part of the blood flow in a beating heart procedure, the pump can provide about 10, 20, 30, 40, 50, 60, 70, 80, or 90% of the total blood flow for the side of the heart in question with the beating heart providing the remainder of the blood flow needed to sustain the patient during the surgery.

What is claimed is:

1. A method for performing beating heart bypass surgery comprising the steps of:

inserting the cannula portion of a pump and cannula system through the tricuspid valve, through the pulmonary valve and a sufficient length into the pulmonary artery to prevent collapse of the right atrium, right ventricle or pulmonary artery when the heart is stressed, lifted or displaced during surgery; and pumping blood from upstream of the pulmonary valve into the pulmonary artery to augment the flow of blood through the pulmonary valve produced by the beating heart.

2. A method for performing beating heart bypass surgery comprising the steps of:

providing a pump having a pump intake port and a pump outflow port;

inserting a first cannula through an incision in the wall of the right atrium such that an inflow port of the first cannula is disposed in the right atrium;

inserting a second cannula through the first cannula such that the second cannula extends through the tricuspid valve, through the pulmonary valve, and a sufficient length into the pulmonary artery, the first and second cannulas serving to prevent collapse of the right atrium, right ventricle and pulmonary artery when the heart is lifted or displaced during surgery;

connecting the pump intake port to the first cannula;

connecting the pump outflow port to the second cannula; and operating the pump to pump blood from the right atrium through the pump and into the pulmonary artery.

3. A method for sustaining sufficient blood flow in the patient during heart surgery comprising the steps of:

inserting the cannula portion of a pump and cannula system through the interior of one side of the heart to extend the cannula into at least one of the pulmonary artery and aorta; and adjusting the pump output during the surgery to provide sufficient blood flow in the patient during the surgery.

4. The method according to claim 3 wherein the blood flow is pulmonary blood flow to the lungs of the patient.

5. The method according to claim 3 wherein the blood flow is circulatory aortic blood flow to the body of the patient.

6. A method according to claim 8 and further, comprising the steps of:

inserting the cannula portion of a right heart support pump and cannula system through the interior of the right side of the heart to extend into the pulmonary artery;

inserting the cannula portion of the left heart support pump and cannula system through the interior of the left side of the heart to extend into the aorta; and adjusting each pump output during the surgery to provide sufficient pulmonary blood flow and sufficient aortic circulatory blood flow in the patient during surgery.

7. A method for performing beating heart surgery which comprises:

inserting in one side of the heart a tubular member adapted to protect the blood flow path through the heart when the portion of the heart having the tubular member is collapsed or kinked; and performing beating heart bypass surgery while the tubular member is in place in the heart.

8. The method according to claim 7 wherein the tubular member is placed in the right side of the heart.

9. The method according to claim 7 wherein the tubular member is placed in the left side of the heart.

10. The method of performing beating heart surgery as in claim 7, wherein the tubular member comprises one of a cannula and a stent.

11. A method for performing beating heart bypass surgery comprising the steps of:

providing a pump and cannula system having an inflow cannula, an outflow cannula, and a blood pump communicatively coupled therebetween for transporting blood from an inflow port formed in the inflow cannula to an outflow port formed in the outflow cannula;

arranging the pump and cannula system such that the inflow port is disposed in the right atrium and the outflow port is disposed in the pulmonary artery; and operating the pump to transport blood from the right atrium to the pulmonary artery and thereby augment the pulmonary blood flow during beating heart bypass surgery.

12. A method of performing beating heart surgery, comprising the step of maintaining at least partial blood flow through a protected blood flow path within a portion of at least one of the vena cava, the right atrium, the right ventricle and pulmonary artery of a beating heart, wherein the step of maintaining at least partial blood flow involves the step of pumping blood through said protected blood flow path by the action of the beating heart.

13. The method of claim 12 and further, wherein said protected blood flow path is established by positioning a conduit within at least one of the vena cava, the right atrium, the right ventricle, and the pulmonary artery.

14. The method of claim 13 and further, wherein said conduit is provided as a stent deployed within at least one of the vena cava and the pulmonary artery.

15. The method of claim 13 and further, wherein said conduit is provided extending through the pulmonary valve and including a fluid inlet aperture disposed within the right ventricle.

16. The method of claim 15 and further, wherein said conduit is introduced through the wall of the right ventricle for passage through the pulmonary valve.

17. The method of claim 16 and further, wherein said conduit is provided with a blocking member for preventing fluid flow through the wall of the right ventricle.

18. The method of claim 15 and further, wherein said conduit is provided extending through the tricuspid valve and including a fluid inlet aperture disposed within the right atrium.

19. The method of claim 18 and further, wherein said conduit is introduced into the right atrium through the wall of the right atrium for passage through the tricuspid valve.

20. The method of claim 19 and further, wherein said conduit is provided with a blocking member for preventing fluid flow through the wall of the right atrium.

21. The method of claim 18 and further, wherein said conduit is introduced through the vena cava for passage into the right atrium.

22. The method of claim 18 and further, wherein said conduit is provided with a valve for preventing fluid back flow from the right ventricle into the right atrium.

23. The method of claim 15 and further, wherein said conduit is provided with a valve for preventing fluid back flow from the pulmonary artery into the right ventricle.

24. The method of claim 13 and further, wherein said conduit is positioned at least partially within the right atrium and extending through the tricuspid valve to pre-load the right ventricle.

25. The method of claim 24 and further, wherein said conduit is provided with a valve for preventing fluid back flow from the right ventricle into the right atrium.

26. The method of claim 24 and further, wherein said conduit is provided having at least one fluid inlet aperture disposed within the right atrium.

27. The method of claim 24 and further, wherein said conduit is maintained in position through the use of a handle member.

28. The method of claim 13 further, wherein said conduit is maintained in position through the use of a handle member.

29. The method of claim 13 and further, wherein said conduit is provided with an inflatable balloon member to facilitate the placement of said conduit within the pulmonary artery.

30. A method of performing beating heart surgery, comprising the step of maintaining at least partial blood flow through a protected blood flow path within a portion of at least one of the vena cava, the right atrium, the right ventricle and pulmonary artery of a beating heart, including the sub-steps of:

providing a generally coaxial cannula assembly having an inner conduit slideably disposed within an outer conduit;

introducing said generally coaxial cannula assembly into a human body such that a distal opening of said outer conduit is positioned in one of the vena cava, the right atrium, and right ventricle, and a distal opening of said inner conduit is positioned in the pulmonary artery, said inner conduit being slideably advanced through said outer conduit such that said inner conduit is positioned through the pulmonary valve and at least partially within the pulmonary artery to establish said protected blood flow path; and pumping blood through said protected blood flow path by the action of a pump communicatively coupled between said outer and inner conduits, said pump transporting blood from at least one of the vena cava, the right atrium, and the right ventricle through the pulmonary valve and into the pulmonary artery.

31. The method of claim 30 and further, wherein said outer conduit is introduced into the right atrium through an aperture formed through the wall of the right atrium.

32. The method of claim 30 and further, wherein said inner conduit is provided with a curved distal portion to facilitate the placement of the inner conduit through the pulmonary valve and into the pulmonary artery.

33. A method of performing beating heart surgery, comprising the step of maintaining at least partial blood flow through a protected blood flow path within a portion of at least one of the left atrium, the left ventricle and aorta of a beating heart, wherein the step of maintaining at least partial blood flow involves the step of pumping blood through said protected blood flow path by the action of the beating heart.

34. The method of claim 33 and further, wherein said protected blood flow path is established by positioning a conduit at least partially within the aorta.

35. The method of claim 34 and further, wherein said conduit is provided extending through the aortic valve with a fluid inlet disposed in the left ventricle.

36. The method of claim 35 and further wherein said conduit is provided extending through the bicuspid valve into the left atrium with a fluid inlet disposed in the left atrium.

37. The method of claim 36 and further, wherein said conduit is provided with at least one valve for preventing the back flow of blood through at least one of the aortic valve and the bicuspid valve.

38. The method of claim 37 and further, wherein said conduit is introduced through the wall of the left atrium for passage into the left ventricle.

39. The method of claim 38 and further, wherein said conduit is provided with a blocking member disposed therein for preventing the flow of blood through the wall of the left atrium.

40. A method of performing beating heart surgery, comprising the step of maintaining at least partial blood flow through a protected blood flow path within a portion of at least one of the left atrium, the left ventricle and aorta of a beating heart, including the sub-steps of:

providing a generally coaxial cannula assembly having an inner conduit slideably disposed within an outer conduit:

introducing said generally coaxial cannula assembly into a human body such that a distal opening of said outer conduit is positioned in one of the left atrium and left ventricle, and a distal opening of said inner conduit is positioned in the aorta, said inner conduit being slideably advanced through said outer conduit such that said inner conduit is positioned through at least one of the aortic valve and the bicuspid valve to establish said protected blood flow path; and pumping blood through said protected blood flow path by the action of a pump communicatively coupled between said outer and inner conduits, said pump transporting blood from at least one of the left atrium and the left ventricle through the aortic valve and into the aorta.

41. The method of claim 40 and further, wherein said outer conduit is introduced into the left atrium through an aperture formed in the wall of the left atrium.

42. A method of performing beating heart bypass surgery which comprises the steps of:

inserting the cannula portion of a pump and cannula system through the tricuspid valve, through the pulmonary valve and a sufficient length into the pulmonary artery to prevent collapse of the right atrium, right ventricle or pulmonary artery when the heart is stressed, lifted or displaced during surgery;

pumping blood from upstream of the pulmonary valve into the pulmonary artery to augment the flow of blood through the pulmonary valve produced by the beating heart; and positioning the heart to provide surgical access to the lateral or posterior heart vessels during beating heart surgery.

43. The method of claim 42, wherein the step of positioning the heart to provide surgical access to the lateral or posterior vessels of the heart during beating heart surgery involves the further sub-step of supporting the heart during surgery.

44. The method of claim 43, wherein the sub-step of supporting the heart during surgery involves the further sub-step of providing a support member for supporting the heart to provide surgical access to the lateral or posterior vessels of the heart.

45. A method of performing beating heart bypass surgery which comprises:

positioning a first conduit through an incision in one of the wall of the vena cava or right atrium;

positioning a second conduit through an incision in the wall of the pulmonary artery;

providing a blood pump having a pump intake port and a pump outflow port;

connecting said pump intake port to said first conduit to remove blood from at least one of the right atrium and vena cava;

connecting said pump outflow port to said second conduit to deposit blood from said blood pump into the pulmonary artery; and pumping blood from the right atrium or vena cava through the pump and into the pulmonary artery during beating heart surgery.

46. The method of claim 45, further comprising the step of supporting the heart during beating heart surgery to provide surgical access to the lateral or posterior heart vessels.

47. The method of claim 46, wherein the step of supporting the heart during surgery involves the further sub-step of providing a support member.

48. The method of claim 47, wherein the support member comprises a cradle assembly.

* * * * *